US012784903B2

(12) United States Patent
Nguyen et al.

(10) Patent No.: US 12,784,903 B2
(45) Date of Patent: Nov. 3, 2026

(54) SYSTEM AND METHOD FOR CLINICAL DECISION SUPPORT

(71) Applicant: Southern California Permanente Medical Group, Pasadena, CA (US)

(72) Inventors: Dinh Nguyen, San Diego, CA (US); Khang Nguyen, Fountain Valley, CA (US)

(73) Assignee: SOUTHERN CALIFORNIA PERMANENTE MEDICAL GROUP, Pasedena, CA (US)

( * ) Notice: Subject to any disclaimer, the term of this patent is extended or adjusted under 35 U.S.C. 154(b) by 0 days.

(21) Appl. No.: 18/781,911

(22) Filed: Jul. 23, 2024

(65) Prior Publication Data

US 2025/0149151 A1 May 8, 2025

Related U.S. Application Data

(60) Provisional application No. 63/596,190, filed on Nov. 3, 2023.

(51) Int. Cl.
*G06Q 10/10* (2023.01)
*G06Q 10/0633* (2023.01)
(Continued)

(52) U.S. Cl.
CPC ......... *G16H 40/20* (2018.01); *G06Q 10/0633* (2013.01); *G16H 10/60* (2018.01); *G16H 20/00* (2018.01); *G16H 80/00* (2018.01)

(58) Field of Classification Search
CPC ...................................................... G06Q 10/10
See application file for complete search history.

(56) References Cited

U.S. PATENT DOCUMENTS

| | | | | |
|---|---|---|---|---|
| 11,488,713 | B2 | 11/2022 | Velez et al. | |
| 2005/0234740 | A1 * | 10/2005 | Krishnan | G16H 50/70 705/7.42 |

(Continued)

FOREIGN PATENT DOCUMENTS

| | | | |
|---|---|---|---|
| CN | 113841171 | A | 12/2021 |
| CN | 112002397 | B | 5/2023 |
| WO | 2022-092409 | A1 | 5/2022 |

OTHER PUBLICATIONS

International Search Report and Written Opinion of the International Searching Authority for PCT/IB2024/058852, dated Jan. 3, 2025, 9 pages.

(Continued)

*Primary Examiner* — Nga B Nguyen
(74) *Attorney, Agent, or Firm* — Pillsbury Winthrop Shaw Pittman LLP

(57) ABSTRACT

A system and method for clinical decision support include a processor configured to receive a clinical service request; parse the clinical service request into a set of semantic tokens, classify the clinical service request according to the type, severity, and urgency of the clinical service request; execute a preliminary triage operation with the semantic tokens to identify a relevant clinical rule and a primary workflow for responding to the clinical service request based on a classification and/or label, the relevant clinical rule and primary workflow are each unique and tailored for a specific medical service provider organization; generate a decision support recommendation based on the relevant clinical rule and primary workflow; and transfer the decision support recommendation to an organizational processing subsystem for the specific medical service provider organization based on the primary workflow.

51 Claims, 15 Drawing Sheets

(51) Int. Cl.

| | |
|---|---|
| ***G16H 10/60*** | (2018.01) |
| ***G16H 20/00*** | (2018.01) |
| ***G16H 40/20*** | (2018.01) |
| ***G16H 80/00*** | (2018.01) |

(56) References Cited

U.S. PATENT DOCUMENTS

| | | | | |
|---|---|---|---|---|
| 2007/0175980 | A1* | 8/2007 | Alsafadi ................ | G16H 50/20<br>235/375 |
| 2009/0177493 | A1* | 7/2009 | Narayan ................ | G06Q 10/10<br>705/3 |
| 2011/0301982 | A1* | 12/2011 | Green, Jr. .............. | G16H 40/67<br>705/3 |
| 2022/0392642 | A1* | 12/2022 | Dasi ........................ | G16H 50/50 |
| 2023/0178193 | A1 | 6/2023 | Vasist et al. | |
| 2024/0186004 | A1* | 6/2024 | Baronov ................ | G16H 50/20 |

OTHER PUBLICATIONS

International Preliminary Report on Patentability (Chapter I) for PCT/IB2024/058852, issued May 5, 2026, transmitted May 15, 2026, 6 pages.

* cited by examiner

SYSTEM AND METHOD FOR CLINICAL DECISION SUPPORT

CROSS-REFERENCE TO RELATED APPLICATION

This application claims priority to U.S. Provisional Patent Application No. 63/596,190, entitled SYSTEM AND METHOD FOR CLINICAL DECISION SUPPORT, filed Nov. 3, 2023, the contents of which are hereby incorporated in their entirety by this reference.

BACKGROUND

Field

The present disclosure is generally related to a method and system for clinical decision support.

Description of Related Art

In the context of clinical service providers, electronic medical records and customer relationship management systems are vital. However, certain shortcomings in current technology impede their full potential. One of the key challenges is the sheer volume of incoming clinical service requests. A lack of an effective means to review and distribute clinical service requests impacts the smooth flow of information, which is critical in ensuring coordination and desirable clinical outcomes.

SUMMARY

It is an aspect of this disclosure to provide a system for clinical decision support. The system may include a processor configured to receive a clinical service request from at least one of an electronic health records system, a patient portal, a call center, a third-party system, and a professional referral. The processor may be further configured to parse the clinical service request into a plurality of semantic tokens that includes clinical metadata for clinical metadata ontology using a machine learning model, clinical knowledge, operational knowledge, and statistical analyses. The processor may be further configured to execute a preliminary triage operation with the plurality of semantic tokens to classify and/or label the clinical service request, a classification and/or label configured to account for both a type of the clinical service request, and/or a varying severity and/or urgency of the clinical service request, and identify at least one relevant clinical rule and at least one primary workflow for responding to the clinical service request based on a classification and/or label, the at least one relevant clinical rule and the at least one primary workflow are each unique and tailored for a specific medical service provider organization. The processor may be further configured to generate at least one decision support recommendation based on the at least one relevant clinical rule and the at least one primary workflow, wherein the decision support recommendation includes recommendations for patient care that account for at least one of medication history, preexisting conditions, information gathered during a doctor visit, and medical data gathered from external sources. The processor may be further configured to transfer the at least one decision support recommendation to a multi-tiered organizational processing subsystem based on the at least one primary workflow, the multi-tiered organizational processing subsystem may be unique and tailored for the specific medical service provider organization, wherein general clinical service requests are addressed by appropriately non-specialized or non-localized remedies found in a lowest tier of the organizational processing subsystem, and wherein specialized clinical service requests may be addressed by remedies found in a highest tier of the organizational processing subsystem, and wherein each tier of the organizational processing subsystem has a dedicated workflow for clinical service requests.

Another aspect provides a method for clinical decision support. The method may include receiving, via a processor, a clinical service request. The method may further include parsing, via the processor, the clinical service request into a plurality of semantic tokens. The method may further include classifying and/or labeling, via the processor, the clinical service request, a classification and/or label configured to account for both a type of the clinical service request, and/or a varying severity and/or urgency of the clinical service request. The method may further include executing, via the processor, a preliminary triage operation with the plurality of semantic tokens to identify at least one relevant clinical rule and at least one primary workflow for responding to the clinical service request based on a classification and/or label, the at least one relevant clinical rule and the at least one primary workflow each being unique and tailored for a specific medical service provider organization. The method may further include generating, via the processor, at least one decision support recommendation based on the at least one relevant clinical rule and the at least one primary workflow. The method may further include transferring, via the processor, the at least one decision support recommendation to an organizational processing subsystem for the specific medical service provider organization based on the at least one primary workflow.

DETAILED DESCRIPTION OF THE EMBODIMENT(S)

A system for clinical decision making enables automatic screening and triage of clinical service requests that are received from a plurality of sources. The term "clinical service request" is used herein to refer to any communication received by a healthcare entity and may refer to at least one of an email, a voice message, a message received through a patient portal, a text message, an automated alert, or a notification from a vendor. The term "healthcare entity" is used herein to refer to medical service provider organizations, medical supply vendors, laboratories, drug manufacturers, and other service providers with a connection to healthcare systems. The clinical service request may refer to a clinical event, message, or request. The healthcare entity may specify what constitutes a clinical service request. For example, the healthcare entity may specify that an alert from an insulin pump or heart rate monitor is classified as a clinical service request. Alternatively, the clinical entity may specify that a notification about a delivery is a clinical service request. The plurality of sources may include at least one of an electronic health records system, a patient portal, a call center, a third-party system, and a professional referral. However, the sources of clinical service requests may be updated and expanded as the requirements of the healthcare entity change.

Figure 1:
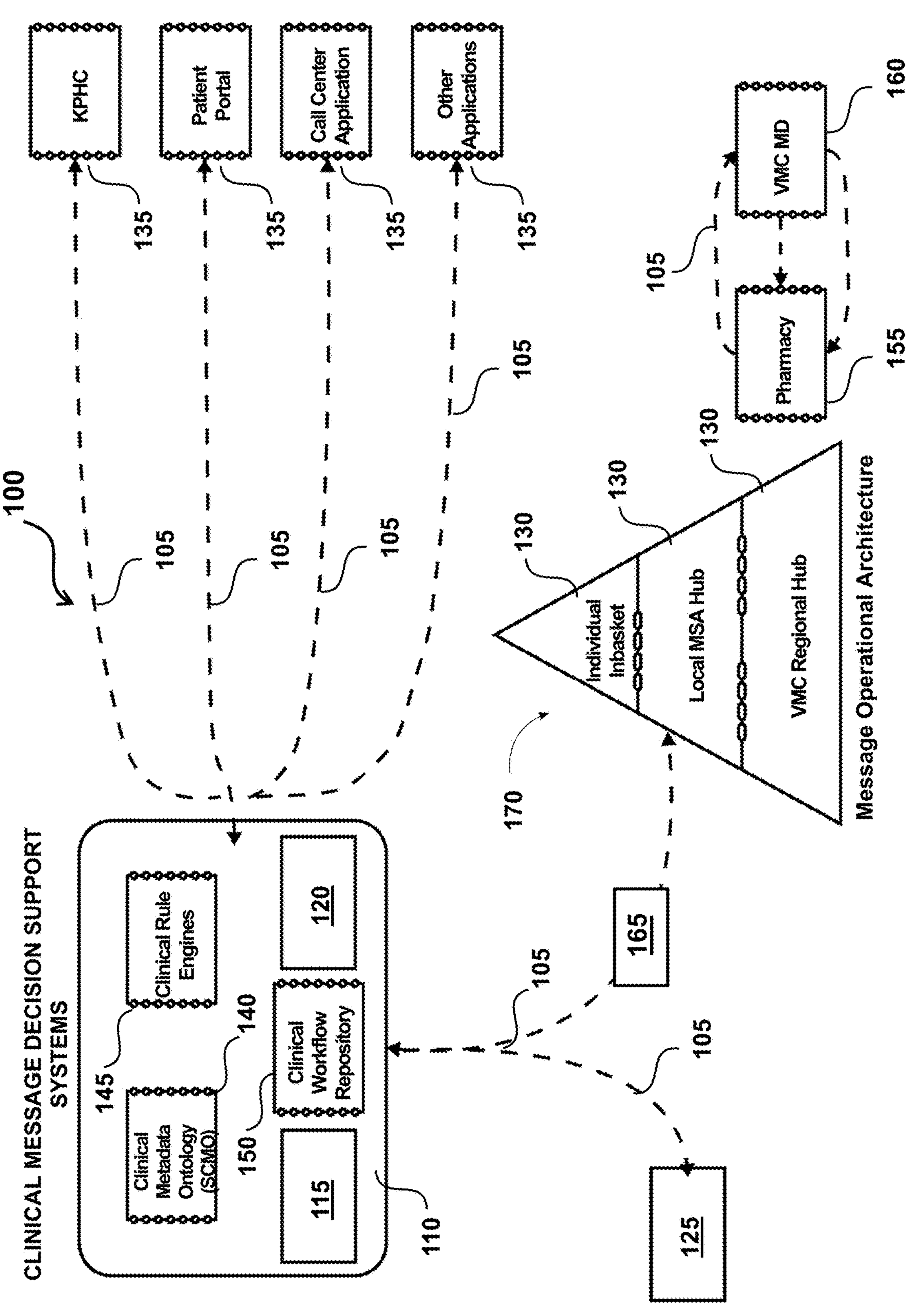
FIG. 1 is a system diagram illustrating connections between components of the system, wherein dashed lines indicate communication over a network, in accordance with embodiments of this disclosure.

Illustrated in FIG. 1, the system 100 may enable the human operators within a healthcare entity to decrease human errors in medicine. Further, the human operators of the healthcare entity may not have sufficient time to adequately respond to each clinical service request because the healthcare entity receives a torrent of clinical service requests from the plurality of sources. The system 100 may include a clinical decision-making support system (CDSS) to reduce the human factors that affect healthcare outcomes. Although clinicians maintain a high knowledge base of medical information, clinicians are human and sometimes may not recognize signals or medical information that suggests a medical condition unrelated to the medical condition for which the patient was admitted. Here, clinician may refer to medical professionals, their support staff, vendors, contract workers, users, consultants or any individual authorized to interact with the system 100. In some embodiments, clinician may refer to any individual interacting with the system 100 (e.g., patients, guardians, caregivers, third party systems). The system 100 is designed to address or reduce human error and oversight in clinical care. For example, the CDSS may remind the human operator to check for continuity of care, schedule follow-up appointments, or to escalate the patient's case. Further, the CDSS increases the overall quality of clinical care by providing a consistent experience for patients and clinicians. Because much of the background research and correlation is provided by the CDSS, the clinician is free to assess the relevant facts and make an informed decision. Note that in FIG. 1 and other figures MD represents an example doctor and/or other medical practitioners/clinicians.

In some embodiments, the system 100 includes a conversational interface 165 that may present the clinician with real-time feedback and prompt the clinician to enter data and requests. The conversational interface 165 may enable the clinician to refine the scope of care based on an iterative process where the clinician asks the CDSS questions and the CDSS provides clinically relevant responses. The clinically relevant responses may incorporate data from multiple sources into recommendations or messages that are presented to the clinician and assist the clinician in arriving at an appropriate plan for clinical care. For example, the conversational interface 165 may include a large language model (LLM) chatbot interface through which the clinician may speak, type, or otherwise input prompts and receive relevant recommendations. Prompts may refer to any input (e.g., queries, patient health data, scheduling information, billing information, clinician specialization information) the clinician wishes to have the CDSS consider and respond to. Further, all interactions the clinician has with the conversational interface 165 may be recorded as interaction data and used to further train the system 100.

FIG. 1 illustrates a network 105, a system server 110, a server processor 115, a communication interface 120, a database 125, processing subsystems 130, clinical interfaces 135, a clinical metadata ontology (SCMO) engine 140 (which defines, recognizes, parses, etc., various clinical metadata ontology words, phrases, etc.), a clinical rules engine 145, a clinical workflow repository 150, a pharmacy 155 (as one example of possible category of a type of medical service that may be provided to a patient), a voicemail call center doctor 160 (VMC MD), and/or other components of the system 100. Each of these components is described in greater detail below.

The system 100 is configured to address an ever-increasing number of clinical service requests received by the healthcare entity. It is not unusual for a healthcare entity to receive tens of thousands of emails a month, each of which could refer to a complex medical issue. Requests are also received in other forms, further adding to the overall quantity of requests. The problems caused by an overabundance of requests are further compounded by the fact that many clinical service requests contain unstructured data that is difficult to analyze and produce meaningful data interpretations. For example, many email requests are written in freeform text that does not clearly enumerate the information a clinician may need to effectively respond to the clinical service request. Further, unstructured requests classified as "other" form the single largest subset of clinical service requests received by medical entities. Accordingly, clinicians are required to spend a considerable amount of time screening clinical service requests and determining the relevant details before transmitting the request to the appropriate individual. This leads to delays in care and providing an appropriate response. As a consequence of the above-described backlog, clinical service requests that should be addressed by a general pool of individuals are frequently transferred to a specialist's inbox where they must be reassessed and rerouted to the appropriate pool of individuals.

Figure 2:
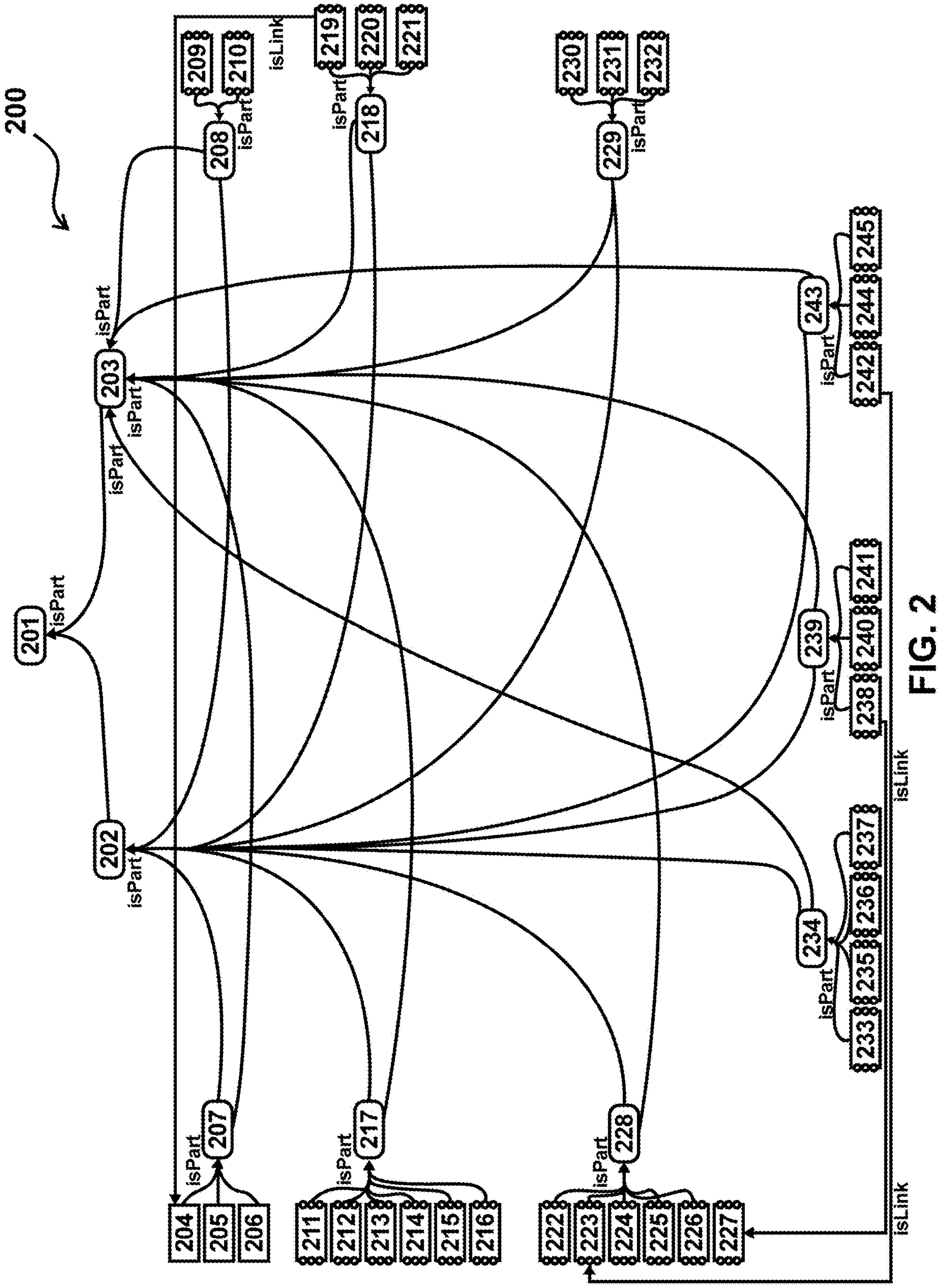
FIG. 2 is a flow chart illustrating how data is sourced from the medical information repository in accordance with embodiments of this disclosure.

As shown in FIG. 2, the system 100 may employ a machine learning model 200 to perform clinical metadata ontology and thereby parse the clinical service requests to identify relevant semantic tokens within the clinical service requests. By way of several examples, FIG. 2 illustrates various potential aspects of an example clinical request including a message summary 201, a call center message 202, a secured message 203, an appointment request 204, appointment questions 205, an appointment follow up 206, an appointment 207, a response 208, thank you language in the response 209, other language in the response 210, first test results 211, second test results 212, third test results 213, fourth test results 214, fifth test results 215, sixth test results 216, a test result summary 217, a symptoms summary 218, symptom red flags 219, a symptoms follow up 220, chronic symptoms 221, first labs 222, second labs 223, third labs 224, fourth labs 225, fifth labs 226, sixth labs 227, a labs summary 228, an immunizations summary 229, a first immunization 230, a second immunization 231, a third immunization 232, a first form 233, a form summary 234, a second form 235, a third form 236, a fourth form 237, a first medication 238, a medication summary 239, a second medication 240, a third medication 241, a first procedure 242, a procedure summary 243, a second procedure 244, and a third procedure 245. As FIG. 2 illustrates, there are many potential aspects to any given clinical services request.

The term "clinical metadata ontology" is used herein to refer to a multi-component protocol for correlating the clinical service request to user-defined features of the healthcare entity's organizational structure including descriptions of semantic tokens relevant to the healthcare entity's unique organizational structure, descriptions of grouping structures for semantic tokens and their relevant attributes, and domain-specific descriptions based on the healthcare entity's specialties and clinical workflow. In some embodiments, the machine learning model may utilize natural language processing models to review and tokenize the clinical service request. Further, the method may make use of clinical knowledge, operational knowledge, logic-based web ontology language translations, ontology-based feature engineering, domain-specific common data elements, ISO/IEC 11179 Metadata Registry standards, and statistical analyses while performing the clinical metadata ontology to identify the appropriate semantic tokens. Additionally, the clinical metadata ontology may employ feature engineering to make heterogeneous clinical data accessible to machine learning models when generating at least one decision support recommendation. To facilitate this functionality, the system may include a feature store where relevant features of the clinical service requests are stored and organized to either train the machine learning algorithm or to make predictions (e.g., the at least one decision support recommendation). The feature store may be used to create or update groups of features created from multiple different data sources or create and update new datasets from those feature groups for training models. In some embodiments, the system 100 makes use of a variety of data sources as input for a machine learning algorithm to build the machine learning model which enables the healthcare entity to execute granular control over how specific service requests are handled in their unique organizational structure. Further, the parsing may identify a severity of the clinical service request such that high-severity requests are processed using a different workflow than low or medium-severity clinical service requests. In some embodiments, the system 100 may generate a knowledge graph that charts relevant information and statistics for the clinical service requests in relation to previously received clinical service requests and other tokens identified during the clinical metadata ontology (FIG. 4B). This knowledge graph may be integrated into an interactive graphical user interface (GUI) 101. Additionally, the GUI 101 may prompt the user to perform a plurality of application-specific data analysis operations. For example, the user may direct the knowledge graph to generate a heatmap that shows the traffic of patients through the hospital. In some embodiments, the system 100 may provide a decision support recommendation that proposes a list of additional staff to employ during peak hours.

In some embodiments, the healthcare entity employs a multi-tiered organizational structure 170 (see the example triangle shape at the center bottom of FIG. 1). The multi-tiered organizational structure 170 may refer to an organization that has multiple departments and/or offices; each of which has a dedicated function and is used to execute at least one step in a workflow for responding to clinical service requests. The hierarchical stratification of the organizational structure is designed to facilitate efficient triage of the inundation of clinical service requests received by the healthcare entity. Specifically, the lower tiers of the organizational structure may be used to respond to general inquiries and issues, thus, leaving the higher tiers of the organizational structure sufficient bandwidth to address clinical service requests that require specialized responses. The multi-tiered organizational structure 170 may be managed by a plurality of organizational processing subsystems 130 that communicate and work to route clinical service requests to the appropriate party (FIG. 1). The term "organizational processing subsystem" may refer to a data management system that the clinical entity uses to receive and respond to clinical service requests. For example, the organizational processing subsystem 130 for a call center may be a client relations management system used to address issues raised in a lowest tier of the organizational structure. Similarly, a pool of available nurses in a hospital may use an electronic medical records management system to monitor patients and track relevant information in an intermediary tier. Further, a medical doctor may use an electronic prescribing system to send prescriptions to a pharmacy from the highest tier. The pharmacy, in turn, may use an additional system to manage prescription requests and drug interaction information. Accordingly, the multi-tiered organizational structure 170 enables the plurality of organizational processing subsystems 130 to communicate relevant information between tiers as well as within the same tier.

Figure 3:
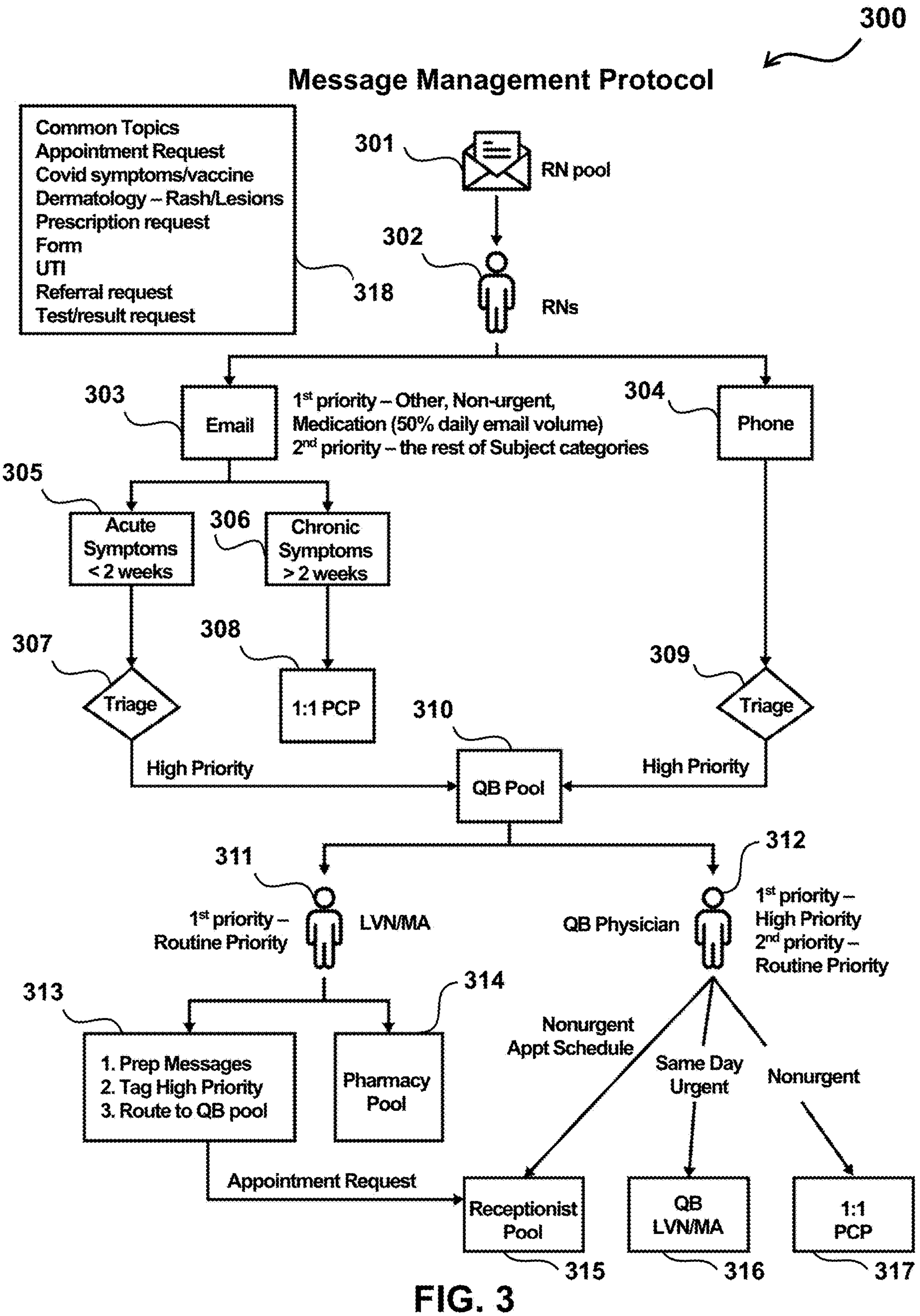
FIG. 3 is a block diagram illustrating a message management protocol for the system of FIG. 1 in accordance with embodiments of this disclosure.

FIG. 3 illustrates an example message management protocol 300. FIG. 3 illustrates a message 301 received by a nurse (RN) pool in this example, a nurse 302 (RN) who reviews message 301, an email message pathway 303, a phone message pathway 304, an acute symptom analysis 305, a chronic symptoms analysis 306, triage 307, a primary care physician (PCP) review 308, triage 309, a reviewer (QB) pool 310, another nurse 311 (LVN/MA) in this example, a reviewing physician 312 (QB physician), routing instructions 313, a pharmacy pool 314 (e.g., for pharmacy related messages as one example), a receptionist pool 315, a nurse reviewer 316 (QB LVN/MA), a primary care physician 317, and a list 318 of common topics for messages. Note that in FIG. 3 and other figures, RN, LVN, and/or MA represents an example nurse, PCP represents a primary care physician, QB represents a coordinating practitioner, and/or other medical practitioners.

Figure 4A:
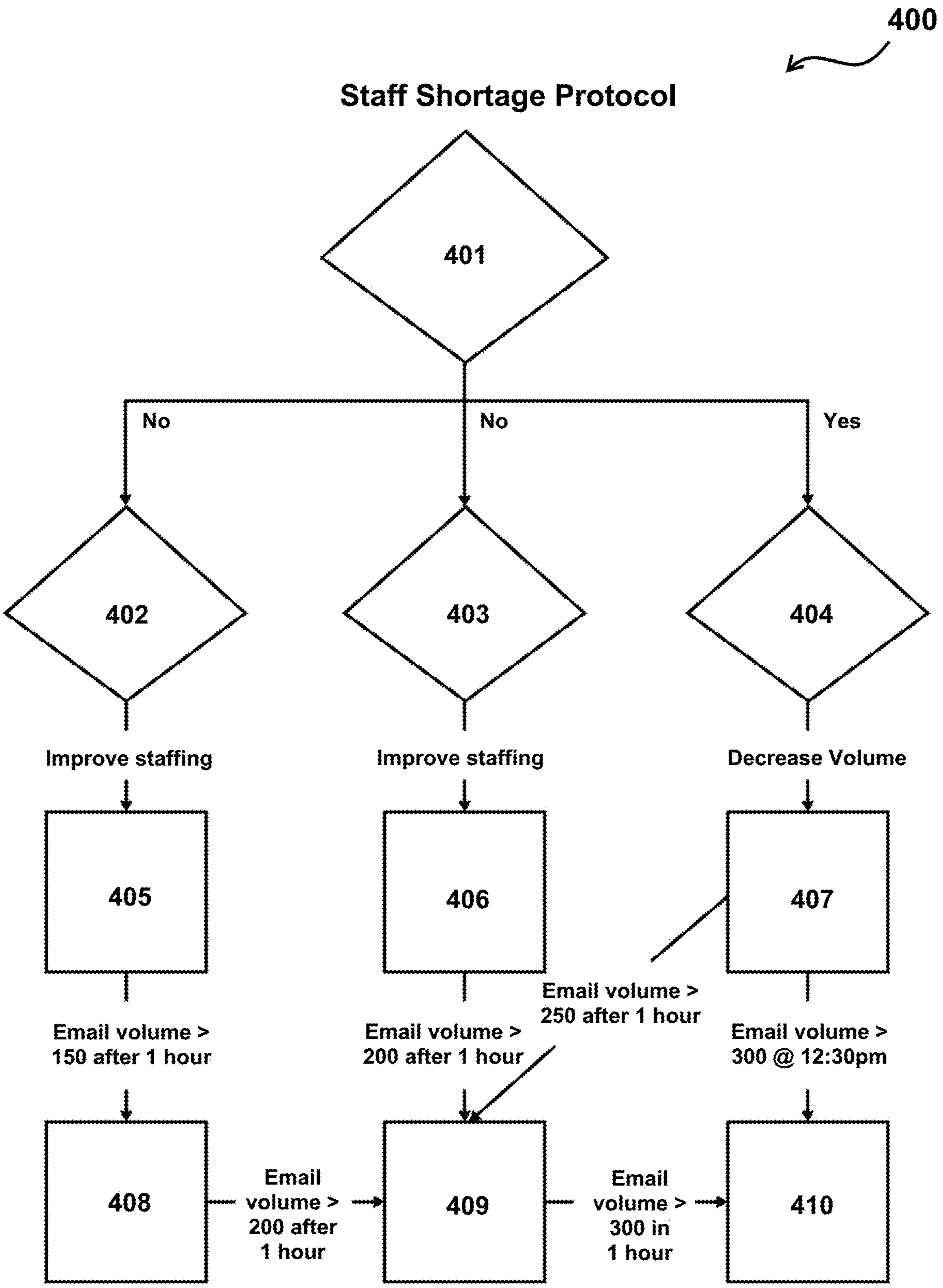
FIG. 4A is a block diagram illustrating a workflow for addressing a staff shortage in accordance with embodiments of this disclosure.
Figure 4B:
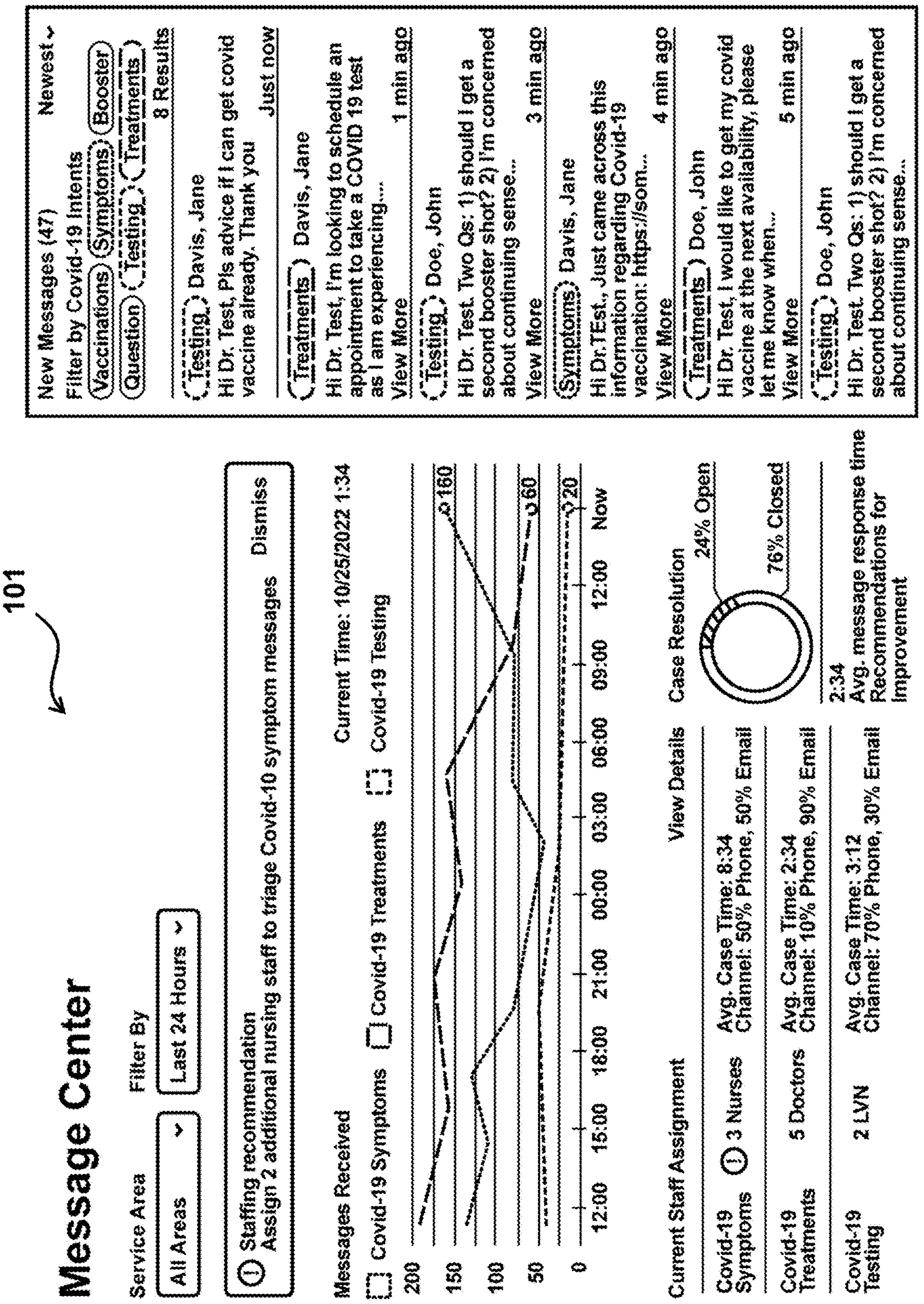
FIG. 4B is a graphical representation of a dashboard for interacting with the system in accordance with embodiments of this disclosure.

As shown in FIG. 1 and FIG. 4A, in some embodiments, a system server 110 may be used to manage the communication, interoperability, and data management operations for the plurality of organizational processing subsystems 130 (FIG. 1). Further, the organizational processing subsystem 130 for a single tier of the overall multi-tiered organizational structure 170 may be used to manage a plurality of secondary subsystems that enable different individuals within the tier to execute specific functions in the primary workflows.

For example, an intermediary tier of the multi-tiered organizational structure 170 may execute a workflow to address a staffing shortage (FIG. 4A). FIG. 4A illustrates a workflow 400 for a staff shortage protocol. In FIG. 4A, 401 indicates a full daily team of nurses and doctors (for this example), 402 indicates no available nurses for emails and a quantity of more than 100 emails at 8:30 am (as an example), 403 indicates an email volume of less than 150 emails at 12:30 pm, 404 indicates an email volume of more than 300 emails at 8:30 am, 405 indicates an addition of a nurse for one hour, 406 indicates an addition of a nurse for one hour, 407 indicates diversion of some messages (e.g., those related to chronic issues may be diverted as opposed to those related to acute issues) by a coordinating doctor, 408 indicates diversion of some messages by the coordinating doctor, 409 indicates the addition of another doctor, 410 indicates prioritization of message response over other non-essential activities performed by the nurses and doctors in this example. Note that the personnel, types of messages, quantities, etc. discussed in FIG. 4A are just representative examples of many possible scenarios.

In a separate example, a prescription received by a pharmacy may first be routed to an inventory manager who determines if the requested drugs are available. The prescription may then be analyzed by the machine learning model to identify adverse drug interactions for the patient before transferring the prescription to a pharmacist for fulfillment. After the prescription has been filled, the primary workflow may stipulate that a message be sent to the patient notifying them that their prescription is ready to be picked up.

Further, notifications and messaging data for the pharmacy may be presented through the GUI 101 (FIG. 4B). FIG. 4B illustrates a dashboard. The dashboard can be AI generated, generated manually, generated automatically by programmed instructions, and/or generated in other ways. FIG. 4B illustrates an example message center GUI for covid related messages. The message center GUI 101 illustrates example fields for a service area, filtering, a staffing recommendation, a graph tracking messages received and other metrics, current staff assignments, case resolution statistics, and thumbnails for several example messages. Note that these fields are representative examples only. Many other possibilities exist.

Figure 5:
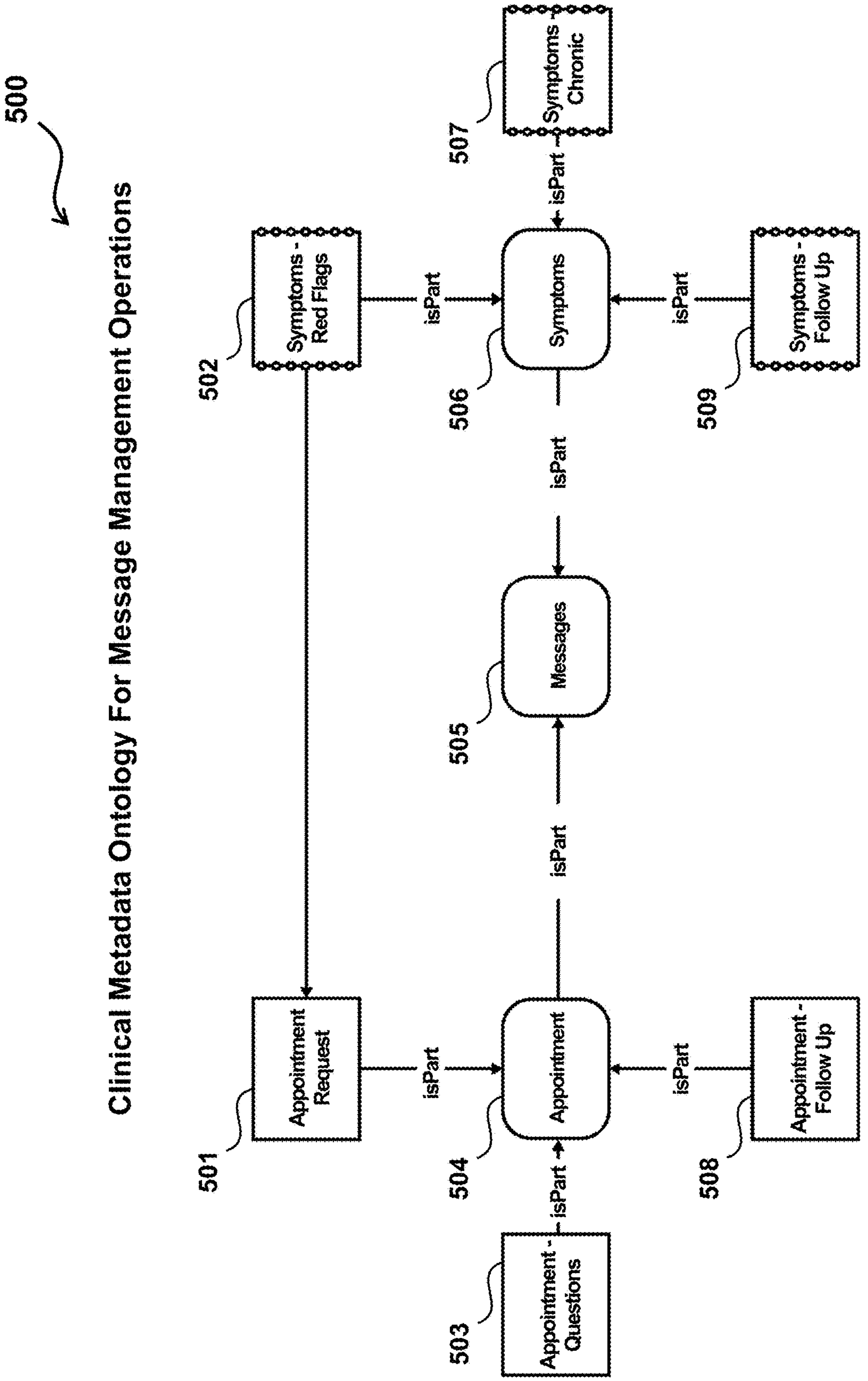
FIG. 5 is a block diagram illustrating a workflow for classifying a message based on type and severity. in accordance with embodiments of this disclosure.

As shown in FIG. 5, the system 100 may execute a preliminary triage operation with the plurality of semantic tokens to classify and/or label the clinical service request, a classification and/or label configured to account for both a type of the clinical service request and/or a varying severity and/or urgency of the clinical service request.

FIG. 5 illustrates example clinical metadata ontology for message management operations 500. FIG. 5 illustrates an appointment request 501, symptoms red flags 502, appointment requests 503, an appointment 504, a message 505, symptoms 506 described in the message, an identification of whether symptoms are chronic 507, an appointment follow up 508, and a symptoms follow up 509. FIG. 5 illustrates the interrelatedness of each of these potential aspects of message 505 and how the present systems and methods use clinical metadata ontology to ensure message 505 with these different aspects is routed most effectively.

In some embodiments, the system 100 may utilize latent semantic analysis (LSA) that uses singular value decomposition (SVD) to scan unstructured clinical service request data to find relevant relationships between 100 million messages received from patients. In some embodiments, the system 100 may utilize latent dirichlet allocation (LDA) to generate a statistical model that facilitates identifying an overall topic for each clinical service request received among millions of clinical service requests. Further embodiments may employ supervised machine learning training and human verification and validation of the clinical service requests and the clinical metadata ontology. In some embodiments, the system 100 may leverage transformer models (e.g., BERT, RoBERTa, DistilBERT, XLNet) and c-TF-IDF to perform NLP operations on the clinical service requests that facilitate generating visualizations of the data which facilitate human consumption and analysis.

Additional embodiments may employ the aforementioned models to generate a classification model from the labeled validated messages so as to incorporate the input from subject matter experts. The classification model may use input from experts, the plurality of semantic tokens, and data gathered while determining and executing the at least one primary workflow as training data to better refine the classification and identification of a message intent for the clinical service request. The intent may refer to a generalized representation of the content of the clinical service request. This generalized representation may enable the system 100 to reduce the processing and latency requirements associated with performing a more in-depth analysis. For example, the classification model may analyze the plurality of semantic tokens to determine that an intended outcome of the clinical service request is related to scheduling an appointment without first determining which clinician or hospital location is specified in the request. The system 100 may then innate an intermediary workflow that may be a subset of the at least one primary workflow required to route the clinical service request to the appropriate level of the multi-tiered organizational structure 170 for further refinement. In some embodiments, the system may employ the conversational interface 165 to refine the intermediary workflow by collecting and analyzing interaction data generated through interactions with the clinician. This process enables system 100 to generate the at least one primary workflow that is both tailored to the unique organizational structure and customized to assist the clinician's unique needs when addressing the clinical service request.

The preliminary triage operation takes the tokenized clinical service request and acts as a front-line clearing house that sorts a plurality of clinical service requests into various classifications and determines if any clinical service requests relate to high-priority issues. For example, the preliminary triage operation may determine that a first clinical service request is a voicemail requesting an appointment and is thus a lower priority than a second clinical service request stating a patient is exhibiting severe symptoms of an unknown illness. In some embodiments, the priority of email and telephone messages received by the RN pool may be arranged thusly:

Priority designations for emails received by an RN:

1. Other/non-urgent emails
2. Test results/questions
3. Past visit questions

Priority designations for telephone messages received by an RN.

1. New appointment request, Same Day, ED follow-ups
2. New medical problem
3. New flu-like symptoms
4. Other (by message date and time, oldest first)

Priority designations for messages delivered to a general in-basket.

Figure 6A:
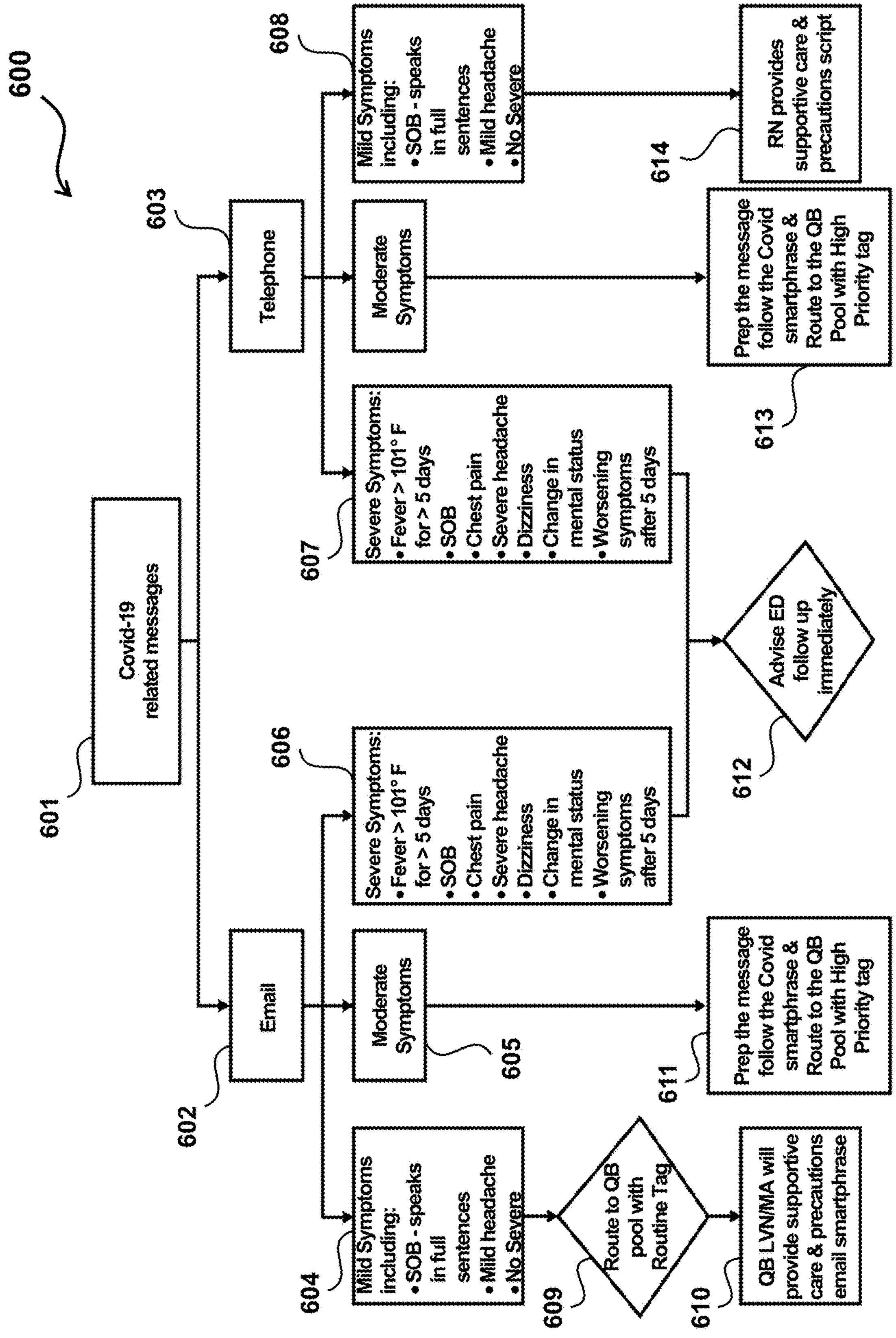
FIG. 6A is a block diagram illustrating a workflow for responding to a message relating to Covid 19 in accordance with embodiments of this disclosure.
Figure 6B:
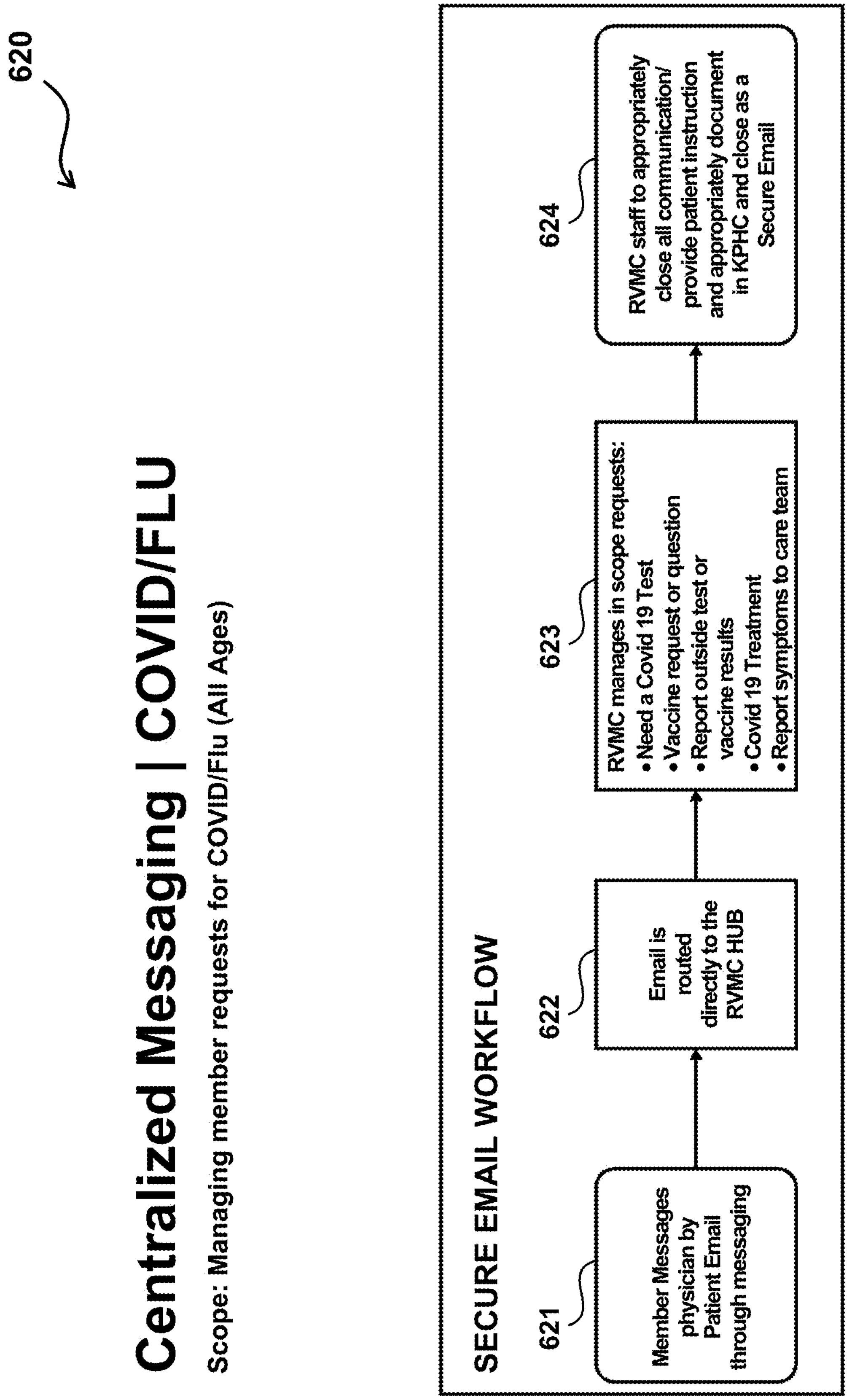
FIG. 6B is a block diagram illustrating a secure messaging workflow in accordance with embodiments of this disclosure.

1. Patient-initiated messages
2. Patient-initiated Emails
3. Provider-initiated messages
4. Staff initiated messages
5. Results notes As shown in FIGS. 6A and 6B, the preliminary triage operation may further identify at least one relevant clinical rule and at least one primary workflow for responding to the clinical service request based on a classification and/or label. The at least one relevant clinical rule may refer to a clinical protocol for responding to the clinical service request. For example, the preliminary triage operation may stipulate specific rules when assessing a clinical service request that relates to a severe infectious disease (e.g., Covid-19, SARS, Ebola). In another example, if an email is received the relevant clinical rule may stipulate that the email first be checked to determine if the contents relate to a patient experiencing acute symptoms for less than two weeks or chronic symptoms for greater than two weeks (FIG. 3). Alternatively, the relevant clinical rule may stipulate that an alert should be generated if a specific patient submits a new request for pain medication. The at least one primary workflow may refer to a protocol for responding to the clinical service request that specifies the steps required to route the clinical service request to an appropriate individual or team within the healthcare entity's organizational structure. For example, the primary workflow may stipulate that voicemail be sent directly to a voicemail call center (VMC) for triage. Alternatively, the primary workflow may stipulate that emails be further processed before determining an appropriate clinical workflow to satisfy the clinical service request. The workflow may further stipulate that the email be compared to a pool of available clinical service providers to determine the best resource for addressing the issue if the content relates to acute symptoms (FIG. 3). In an embodiment, the primary workflow may specify that the clinical service request be delivered directly to a physician's mailbox. The relevant clinical rule and the primary workflow are each unique to and tailored for a specific medical service provider organization.

FIG. 6A is a block diagram illustrating an example workflow 600 for responding to a message 601 relating to Covid 19. FIG. 6A illustrates an email 602, a telephone call 603, a listing of example mild symptoms 604 that may be described in email 602, an indication of moderate symptoms 605 that may be described in email 602, a listing of severe symptoms 606 that may be described in email 602, a listing of severe symptoms 607 that may be described in telephone call 603, an indication of moderate symptoms that may be described in telephone call 603, a listing of example mild symptoms 608 that may be described in telephone call 603, a routing step 609 to a coordinator, a routing step 610 and 614 to a coordinating nurse for a response, a routing step 611 and 613 for a more substantial response, and a routing step 612 for an immediate response.

FIG. 6B is a block diagram illustrating an example secure messaging workflow 620 related to a covid/flu message. FIG. 6B illustrates an email message 621 received by a physician through a messaging portal, email routing 622 (e.g., after analysis as described herein), a coordinator determining needed steps 623 in response to what is described in message 621, and directions 624 for responding to the message.

Figure 7:
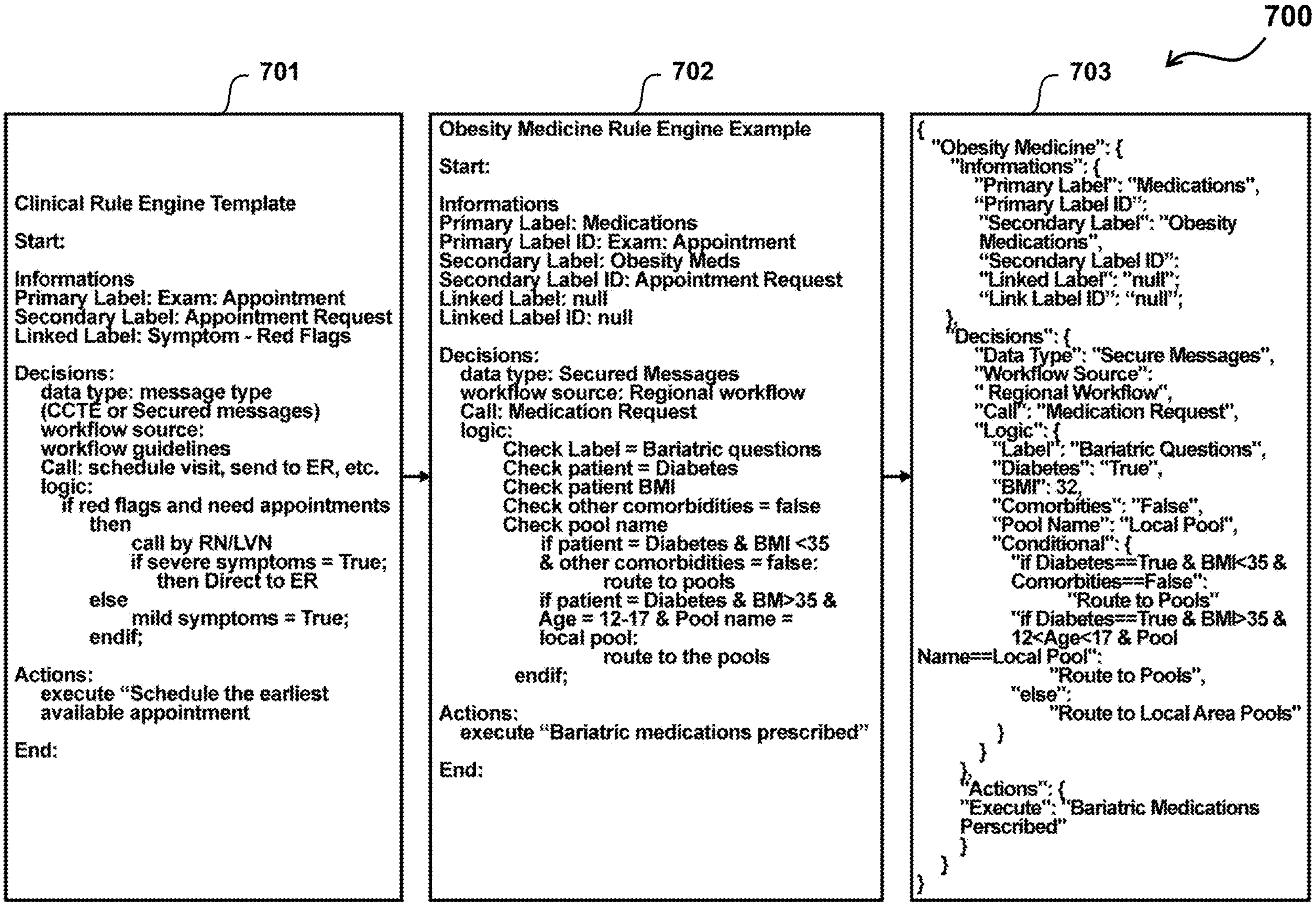
FIG. 7 illustrates an example decision support recommendation in accordance with embodiments of this disclosure.

FIG. 7 illustrates a clinical rule engine template 701, an example obesity medicine rule engine template 702, and a related workflow 703. As shown in FIG. 7, the system 100 (FIG. 1) may generate at least one decision support recommendation 700 based on the at least one relevant clinical rule and the at least one primary workflow. In some embodiments, the system 100 may use semantic parsing techniques to analyze the clinical service requests (e.g., Zero-Shot Task-Oriented Semantic Parsing, a response driven learning framework capable of exploiting feedback based on the response, flexible semantic parsing models, task-oriented dialog systems, deep learning architectures, and conversational semantic parsing). The decision support recommendation may be a report or summary of relevant facts that enable clinical personnel to address the clinical service request without needing to search for additional resources. In some embodiments, the decision support recommendation includes recommendations for patient care that account for at least one of medication history, preexisting conditions, information gathered during a doctor visit, and medical data gathered from external sources. In some embodiments, the decision support recommendation may direct a medical service vendor to provide additional medical supplies due to an unanticipated spike in demand from their customers.

Returning to FIG. 1, the system 100 may transfer the at least one decision support recommendation to a multi-tiered organizational processing subsystem 130 based on the at least one primary workflow. The recipient of the decision support recommendation will be presented with a pre-populated report providing potential remedies to the clinical service request. In some embodiments, the organizational structure of the clinical entity may relate to a healthcare entity that employs a hierarchical organizational structure where triage for clinical service requests is intended to route the majority of requests to the lowest tier of the organizational structure where general requests and services can be performed without significant medical expertise (FIG. 1 and FIG. 3). For example, the lowest tier of the organizational structure may be a regional level grouping that includes voicemail and call centers, billing centers, administrative centers, community outreach programs, and other organization-specific subcategories. In one embodiment, a patient message requesting an appointment may be routed to the lowest tier of the organizational structure. In a further embodiment, questions about billing and general inquiries may also be routed to the lowest tier.

The organizational structure may further include at least one intermediary tier that relates to a local hub of available medical resources capable of performing more specialized tasks. For example, the intermediary tier may refer to a group of registered nurses (RN) working in a specific medical service provider's office. The intermediary tier may be the destination for clinical service requests that require some degree of expertise but may still be responded to by a general group of individuals. For example, any one of a pool of RN in a pediatrician's office may respond to general inquiries about the health of a child. In some embodiments, the intermediary tier may refer to a pool of prescribers who are available to see new patients or who are on call. The highest tier of the organizational structure may relate to the mailboxes of specific individuals within the organization.

Thus, clinical service requests that require the attention of a specific individual or specialist may be delivered directly to the individual's mailbox.

The multi-tiered organizational processing subsystem 130 may be unique and tailored for the specific medical service provider organization, wherein general clinical service requests are addressed by appropriately non-specialized or non-localized remedies found in the lowest tier of the organizational processing subsystem 130, and wherein specialized clinical service requests may be addressed by remedies found in the highest tier of the organizational processing subsystem 130, and wherein each tier of the organizational processing subsystem 130 has a dedicated workflow for clinical service requests The primary workflow may include additional sub-workflows that are executed within a tier of the organizational structure. That is, the primary workflow may denote further triage and message routing based on the available resources within a specific organizational tier or across multiple organizational tiers. For example, a clinical service request related to billing may be first routed to the billing center in the lowest tier, the clinical service request may then be routed directly to the mailbox of the healthcare entity's financial aid manager to assess if a patient qualifies for financial assistance.

Figure 8:
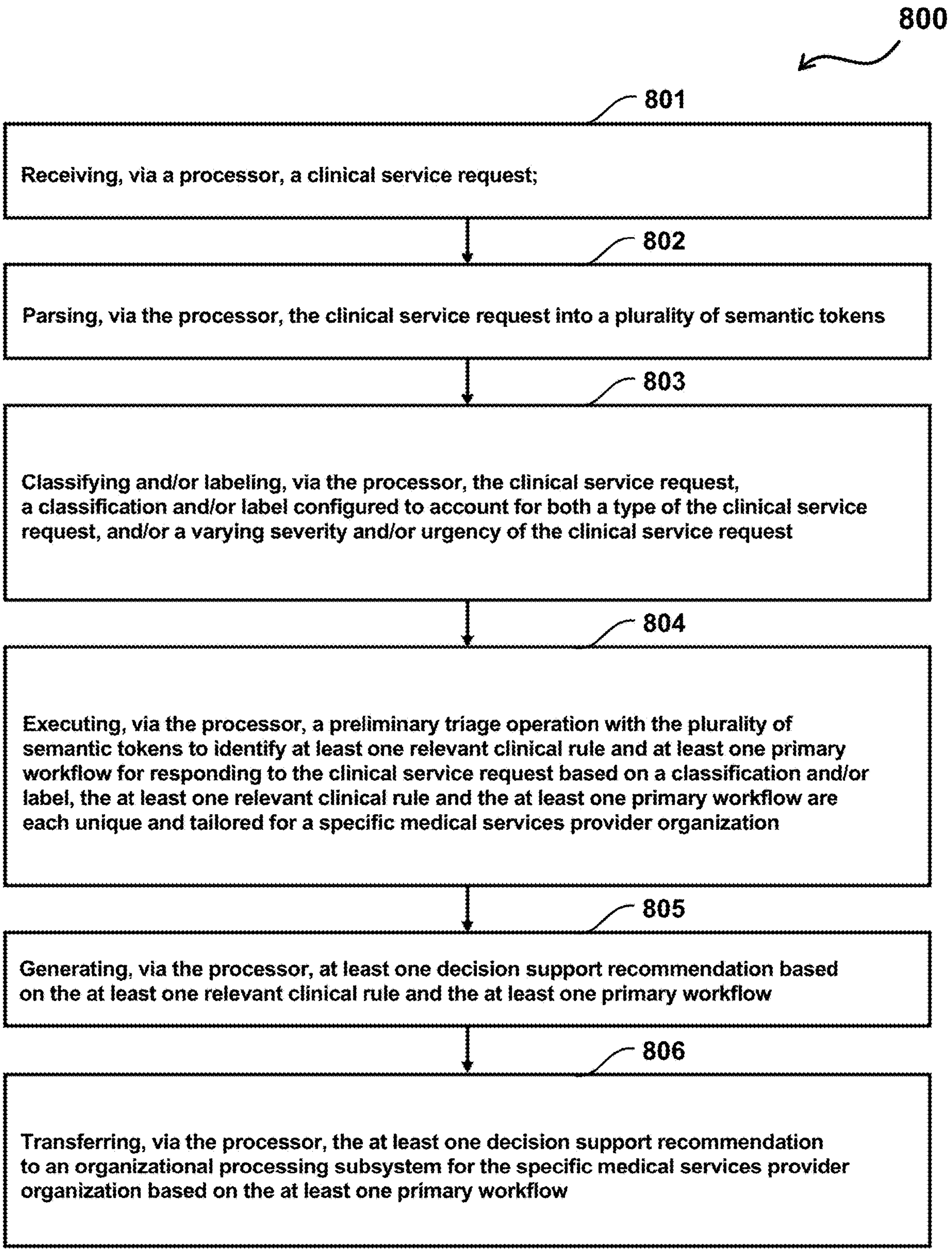
FIG. 8 is a block diagram illustrating an overall method of the disclosed concept in accordance with embodiments of this disclosure.

As shown in FIG. 8, in some embodiments a method 800 for implementing the above-described clinical decision support system may begin by receiving, via a processor, a clinical service request (801). The processor may refer to a computing device capable of performing the operations required to execute the method 800 of the disclosed concept. For example, the processor may refer to a smartphone, a desktop or tablet PC, a system server or data center, or a cloud computing system. The method 800 may continue by parsing, via the processor, the clinical service request into a plurality of semantic tokens (802). At 803, the method 800 may continue by classifying and/or labeling with the classification model, via the processor, the clinical service request, a classification and/or label configured to account for both a type of the clinical service request and/or a varying severity and/or urgency of the clinical service request (FIG. 6A). The classification may relate to the type of clinical service request received. For example, the classification may be an email, a phone call, an appointment request, or a prescription refill request. Accordingly, an email requesting a general physical examination will be of lower severity than a notification that a patient has entered cardiac arrest. The method 800 may continue by executing, via the processor, a preliminary triage operation with the plurality of semantic tokens to identify at least one relevant clinical rule and at least one primary workflow for responding to the clinical service request based on a classification and/or label, the at least one relevant clinical rule and the at least one primary workflow may each be unique and tailored for a specific medical service provider organization (804). The method 800 may continue by generating, via the processor, at least one decision support recommendation based on the at least one relevant clinical rule and the at least one primary workflow (805). The method 800 may continue by transferring, via the processor, the at least one decision support recommendation to an organizational processing subsystem 130 for the specific medical service provider organization based on the at least one primary workflow (806).

The method 800 may include a subprocess for parsing the clinical service request into the plurality of semantic tokens. The subprocess may be performed using a machine learning model, clinical knowledge, operational knowledge, and statistical analyses. Further, the parsing may be one such parsing among millions of other clinical service requests and may be based on prior parsing of millions of prior clinical service requests. Accordingly, the machine learning algorithm that builds the machine learning model for semantic tokenization uses the previous parsing as training data to identify semantic tokens, thereby improving the accuracy of message routing and workflow generation. Further, the more clinical service requests that are input for the machine learning algorithm the more adept at parsing, classifying, and routing the clinical service requests for the unique organizational structure the machine learning model becomes. The plurality of semantic tokens includes clinical metadata for clinical metadata ontology. The clinical metadata ontology may be used for describing clinical operations for the medical service provider organization, describing grouping structures for semantic tokens and associated attributes, and generating domain-specific descriptions based on specialties and a workflow associated with the medical service provider organization.

In some embodiments, the plurality of semantic tokens includes at least one token that is associated with a type, a severity, an urgency, a service identifier, and clinical content of the clinical service request The clinical content may refer to relevant information for processing the clinical service request including descriptions of the patient's symptoms, medication history, and drug allergies. The method 800 may include a subprocess for identifying the clinical rule that begins by reviewing, via the processor, the clinical content with a clinical rules engine to determine the at least one relevant clinical rule (FIG. 7). The clinical rules engine is a subprocess within the machine learning model used to correlate tokenized content from the clinical service request to specific medical protocols and procedures. The clinical rules engine may use the tokenized content to search a clinical workflow repository associated with the specific medical service provider organization to identify the at least one primary workflow based on the clinical content and the at least one relevant clinical rule. The clinical workflow repository may be a database that includes a collection of organization-specific workflows that may pertain to at least one of routing protocols, prescriber preferences, regulatory information, clinical diagnostic data, patient data, hospital staff information, insurance data, and contact information. The relevant clinical rule may relate to a specific diagnostic recommendation that is relevant to information within a patient's medical history. For example, if the patient data indicates the patient is being prescribed obesity medication, then the relevant clinical rule may suggest the prescriber ask the patient a series of bariatric questions, check the patient for diabetes, check the patient's body mass index (BMI), and to check for other comorbidities. The clinical rules engine may identify a plurality of relevant clinical rules based on information in the clinical service request and information stored in the clinical workflow repository. Further, the clinical rules engine may identify additional workflows to recommend to the prescriber based on information in the clinical service request, information stored in the clinical workflow repository, and the structure of the multi-tiered organization subsystem 130. For example, the physician may be presented with a set of secondary actions to take depending on the patient's diabetes diagnosis and BMI. In some embodiments, the machine learning model may be used for reviewing with the clinical rules engine and searching the clinical workflow repository to enable improved semantic tokenization and workflow selection.

In some embodiments, the service identifier is included as criteria in the search to identify the at least one primary workflow, and the service identifier may denote at least one of an appointment request, a medication refill request, referral questions, lab test results, imaging results, a symptom question, a procedure question, a form request, an immunization question, an obesity medication questions, a personal health information update, and an indication of where a patient or a patient's proxy (e.g., spouse, parent, child, etc.) is in a medical service progression (e.g., whether the patient was seen for a chest pain workup and needed an outpatient follow up or is this a new chest pain?). Further, the list of available service identifiers may change and be updated based on clinical operations, patient behavior, and any emergent medical needs of patients.

In some embodiments, a plurality of organizational processing subsystem 130 is arranged into a multi-tiered response hierarchy (FIG. 1). The organizational processing subsystem 130 may be an electronic medical records system used by the medical service provider's office. In some embodiments, the organizational processing subsystem 130 may be a device used to relay information between clinical personnel and the system 100. In further embodiments, the multi-tiered organizational processing subsystem 130 may be unique and tailored for the specific medical service provider organization. Additionally, the lowest tier of the response hierarchy is generally tasked with responding to clinical service requests denoted by service identifiers directed toward satisfying general service requests, and each tier in a plurality of subsequent tiers of the organizational processing subsystem 130 is directed to an increasingly specialized group of possible respondents.

In some embodiments, the multi-tiered organizational processing subsystem 130 is configured to process clinical service requests, depending on how various respondents or groups of respondents associated with the multi-tiered organizational processing subsystem 130 are defined. For example, the clinical service requests may be processed in a hierarchical manner, in an inter-tier or direct manner, skipping one or more tiers of the multi-tiered organizational processing subsystem 130 depending on the nature of a clinical service request, in an intra-tier transfer manner between multiple respondents within the same tier level (e.g., within the VMC hubs, and for practice-specific mailboxes such as pharmacists, physicians, licensed vocational nurse (LVN), RN. The clinical service request may be transferred from one LVN pool to another pool of respondents (e.g., a clinical service provider) if the clinical service request necessitates further triage and/or in a dynamic manner up and/or down the multi-tiered organizational processing subsystem 130 depending on a medical service progression for the clinical service request. For example, multiple RN and/or LVN may be attending to a patient during convalescence. In this example clinical service requests may be transferred between individuals within the same tier of the organizational processing subsystem 130 to enable the RN and/or LVN to discuss the patient's status among themselves and have all relevant service requests consolidated and accessible by the relevant RN and/or LVN.

In some embodiments, the multi-tiered organizational processing subsystem 130 may be managed by multiple providers with different scopes of practice that are defined by local and/or state regulations (e.g., Physicians can do certain things that RN cannot do, and RN can do certain things that LVN cannot do). In further embodiments, the decision support recommendation is transferred directly into an individual's mailbox for processing at the highest tier of the multi-tiered organizational processing subsystem 130. Accordingly, the system 100 facilitates vital information to the individual who most needs it. Further, the clinical rules engine enables adaptive filtering to prevent a significant number of irrelevant clinical service requests from cluttering the clinical service provider's mailbox.

The decision support recommendation may be transferred to a regional hub for processing at the lowest tier of the multi-tiered organizational processing subsystem 130. Further, the decision support recommendation may be transferred to a processing pool for at least one intermediary tier of the multi-tiered organizational processing subsystem 130. In some embodiments, the intermediary tier processing pool may include a pharmacy pool, a prescriber pool, a receptionist pool, a medical assistant and/or vocational nurse pool, an administrative pool, a form pool, a local medical service pool, a subspecialty pool, and/or a behavioral health pool. Further, the list of processing pools in any tier of the multi-tiered organizational substructure may be changed or updated based on the needs of the clinical service provider. In further embodiments, the clinical service request is received from at least one clinical interface 135. In some embodiments, the at least one clinical interface 135 may be a communication system used to relay information between the patient and the system 100 (e.g., an electronic health records system, a patient portal, a call center, a third-party system, and a professional referral) (FIG. 1). In some embodiments, the system 100 includes an operational dashboard that is configured to track (e.g., archive, analyze, share, and/or tokenize) outputs (e.g., to electronic health records, pharmacy systems, or other locations) associated with clinical service requests. In some embodiments, the system 100 incorporates the operational dashboard into a graphical user interface. Additionally, the operational dashboard may provide a user with an up-to-date view of the data being processed by the system 100. Specifically, the operational dashboard may be configured for real-time updates and updates over any user-defined time interval (e.g., minute by minute, hourly, shift by shift, daily, weekly, and/or monthly) to facilitate resource allocation by the medical service provider organization. Further, the operational dashboard may enable the user to send and receive clinical service requests and may act as a terminal to enable the user to implement all features of the system 100 available to the user's medical service provider organization.

In some embodiments, the system server 110 may be any suitable computing device and/or data processing apparatus capable of communicating with computing devices, other remote devices (e.g., mobile health screening devices, telehealth systems, and patient monitoring devices) or computing networks (e.g., the plurality of organizational processing subsystems 130), receiving, transmitting, and storing electronic information and processing requests as further described herein. System server 110 is therefore intended to represent various forms of digital computers, such as laptops, desktops, workstations, personal digital assistants, servers, blade servers, mainframes, and other appropriate computers and/or networked or cloud-based computing systems capable of employing the systems and methods described herein.

System server 110 may include a server processor 115, which is communicably coupled to various hardware and software components that serve to enable operation of the system 100. For example, system server 110 may be positioned external to the plurality of organizational processing subsystems 130 and act as a remote data center coordinating the operation of a multi-tiered organizational structure 170 that is distributed across a large geographic area.

Additionally, the system server 110 may be capable of communicating with additional external systems through communications network 105. Server processor 115 serves to execute instructions to perform various operations relating to triaging clinical service requests, providing decision support, managing the machine learning algorithm and model, and other functions of embodiments of the disclosed devices as described in greater detail herein. For example, server processor 115 may respond to a request for a list of approved medications by retrieving the list from the medical information repository or a database connected to network 105. Server processor 115 may be one or a number of processors, a central processing unit (CPU), a graphics processing unit (GPU), a multi-processor core, or any other type of processor, depending on the particular implementation.

System server 110 may be configured to communicate via a communication interface 120 with various other devices (database 125) connected to network 105. For example, the communication interface 120 of system server 110 may include but is not limited to, a modem, a Network Interface Card (NIC), an integrated network interface, a radio frequency transmitter/receiver (e.g., Bluetooth wireless connection, cellular, Near-Field Communication (NFC) protocol, a satellite communication transmitter/receiver, an infrared port, a USB connection, and/or any other such interfaces for connecting the system server 110 to other computing devices and/or communications networks 105 such as private networks and the Internet. In an embodiment, system server 110 may use network 105 to communicate with a database 125 for data retrieval and storage. In an embodiment, system server 110 may use network 105 to communicate with an emergency response system whenever an emergency event is detected within a clinical service request. In an embodiment, system server 110 may use network 105 to function as a cloud data center capable of analyzing data collected from the plurality of organizational processing subsystems 130 to perform clinical data management operations, including determining the relevant clinical rule, generating the primary workflow, managing the machine learning model, and coordinating communications.

Figure 9:
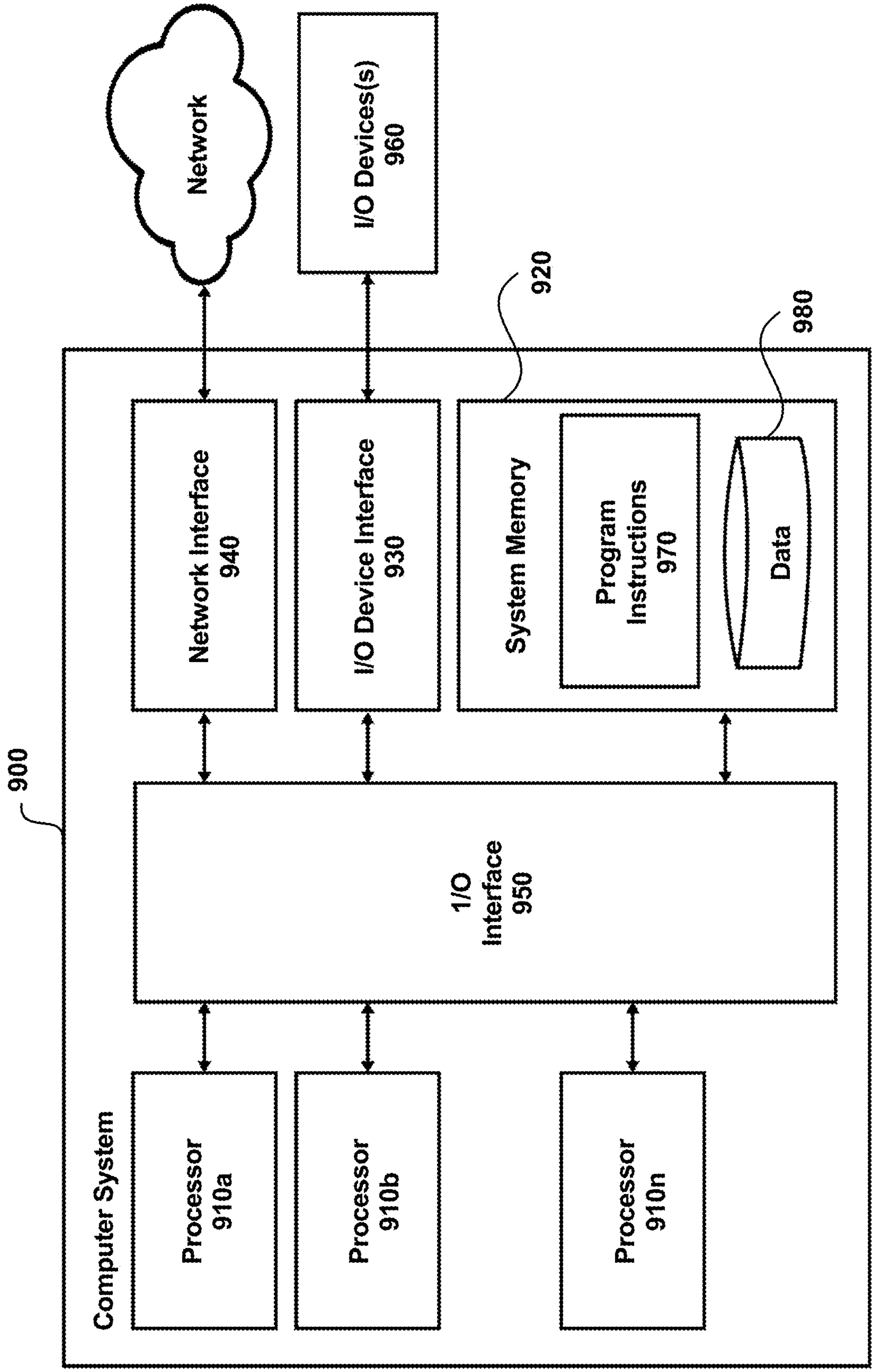
FIG. 9 is a diagram that illustrates an exemplary computing system in accordance with embodiments of this disclosure.

FIG. 9 is a diagram that illustrates an exemplary computer system 900 in accordance with embodiments of the present system. Various portions of systems and methods described herein may include or be executed on one or more computer systems the same as or similar to computer system 900. For example, components of the system 100 (FIG. 1) may be and/or include one or more computer systems the same as or similar to computer system 900. Further, processes, modules, processor components, and/or other components of system 100 described herein may be executed by one or more processing systems similar to and/or the same as that of computer system 900.

Computer system 900 may include one or more processors (e.g., processors 910*a*-910*n*) coupled to system memory 920, an input/output I/O device interface 930, and a network interface 940 via an input/output (I/O) interface 950. A processor may include a single processor or a plurality of processors (e.g., distributed processors). A processor may be any suitable processor capable of executing or otherwise performing instructions. A processor may include a central processing unit (CPU) that carries out program instructions to perform the arithmetical, logical, and input/output operations of computer system 900. A processor may execute code (e.g., processor firmware, a protocol stack, a database management system, an operating system, or a combination thereof) that creates an execution environment for program instructions. A processor may include a programmable processor. A processor may include general or special purpose microprocessors. A processor may receive instructions and data from a memory (e.g., system memory 920). Computer system 900 may be a uni-processor system including one processor (e.g., processor 910*a*), or a multi-processor system including any number of suitable processors (e.g., 910*a*-910*n*). Multiple processors may be employed to provide for parallel or sequential execution of one or more portions of the techniques described herein. Processes, such as logic flows, described herein may be performed by one or more programmable processors executing one or more computer programs to perform functions by operating on input data and generating corresponding output. Processes described herein may be performed by, and apparatus can also be implemented as, special purpose logic circuitry, e.g., an FPGA (field programmable gate array) or an ASIC (application specific integrated circuit). Computer system 900 may include a plurality of computing devices (e.g., distributed computer systems) to implement various processing functions.

I/O device interface 930 may provide an interface for connection of one or more I/O devices 960 to computer system 900. I/O devices may include devices that receive input (e.g., from a user) or output information (e.g., to a user). I/O devices 960 may include, for example, graphical user interface presented on displays (e.g., a cathode ray tube (CRT) or liquid crystal display (LCD) monitor), pointing devices (e.g., a computer mouse or trackball), keyboards, keypads, touchpads, scanning devices, voice recognition devices, gesture recognition devices, printers, audio speakers, microphones, cameras, or the like. I/O devices 960 may be connected to computer system 900 through a wired or wireless connection. I/O devices 960 may be connected to computer system 900 from a remote location. I/O devices 960 located on a remote computer system, for example, may be connected to computer system 900 via a network and network interface 940.

Network interface 940 may include a network adapter that provides for connection of computer system 900 to a network. Network interface 940 may facilitate data exchange between computer system 900 and other devices connected to the network. Network interface 940 may support wired or wireless communication. The network may include an electronic communication network, such as the Internet, a local area network (LAN), a wide area network (WAN), a cellular communications network, or the like.

System memory 920 may be configured to store program instructions 970 or data 980. Program instructions 970 may be executable by a processor (e.g., one or more of processors 910*a*-910*n*) to implement one or more embodiments of the present techniques. Instructions 970 may include modules and/or components of computer program instructions for implementing one or more techniques described herein with regard to various processing modules and/or components. Program instructions may include a computer program (which in certain forms is known as a program, software, software application, script, or code). A computer program may be written in a programming language, including compiled or interpreted languages, or declarative or procedural languages. A computer program may include a unit suitable for use in a computing environment, including as a stand-alone program, a module, a component, or a subroutine. A computer program may or may not correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one or more computer processors located locally at one site or distributed across multiple remote sites and interconnected by a communication network.

System memory 920 may include a tangible program carrier having program instructions stored thereon. A tangible program carrier may include a non-transitory computer readable storage medium. A non-transitory computer readable storage medium may include a machine readable storage device, a machine readable storage substrate, a memory device, or any combination thereof. Non-transitory computer readable storage medium may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. System memory 920 may include a non-transitory computer readable storage medium that may have program instructions stored thereon that are executable by a computer processor (e.g., one or more of processors 910*a*-910*n*) to cause the subject matter and the functional operations described herein. A memory (e.g., system memory 920) may include a single memory device and/or a plurality of memory devices (e.g., distributed memory devices). Instructions or other program code to provide the functionality described herein may be stored on a tangible, non-transitory computer readable media. In some cases, the entire set of instructions may be stored concurrently on the media, or in some cases, different parts of the instructions may be stored on the same media at different times, e.g., a copy may be created by writing program code to a first-in-first-out buffer in a network interface, where some of the instructions are pushed out of the buffer before other portions of the instructions are written to the buffer, with all of the instructions residing in memory on the buffer, just not all at the same time.

I/O interface 950 may be configured to coordinate I/O traffic between processors 910*a*-910*n*, system memory 920, network interface 940, I/O devices 960, and/or other peripheral devices. I/O interface 950 may perform protocol, timing, or other data transformations to convert data signals from one component (e.g., system memory 920) into a format suitable for use by another component (e.g., processors 910*a*-910*n*). I/O interface 950 may include support for devices attached through various types of peripheral buses, such as a variant of the Peripheral Component Interconnect (PCI) bus standard or the Universal Serial Bus (USB) standard.

Embodiments of the techniques described herein may be implemented using a single instance of computer system 900 or multiple computer systems 900 configured to host different portions or instances of embodiments. Multiple computer systems 900 may provide for parallel or sequential processing/execution of one or more portions of the techniques described herein.

Those skilled in the art will appreciate that computer system 900 is merely illustrative and is not intended to limit the scope of the techniques described herein. Computer system 900 may include any combination of devices or software that may perform or otherwise provide for the performance of the techniques described herein. For example, computer system 900 may include or be a combination of a cloud-computing system, a data center, a server rack, a server, a virtual server, a desktop computer, a laptop computer, a tablet computer, a server device, a client device, a mobile telephone, a personal digital assistant (PDA), a mobile audio or video player, a game console, a vehicle-mounted computer, a television or device connected to a television (e.g., Apple TV™), or a Global Positioning System (GPS), or the like. Computer system 900 may also be connected to other devices that are not illustrated, or may operate as a stand-alone system. In addition, the functionality provided by the illustrated components may in some embodiments be combined in fewer components or distributed in additional components. Similarly, in some embodiments, the functionality of some of the illustrated components may not be provided or other additional functionality may be available.

Figure 10:
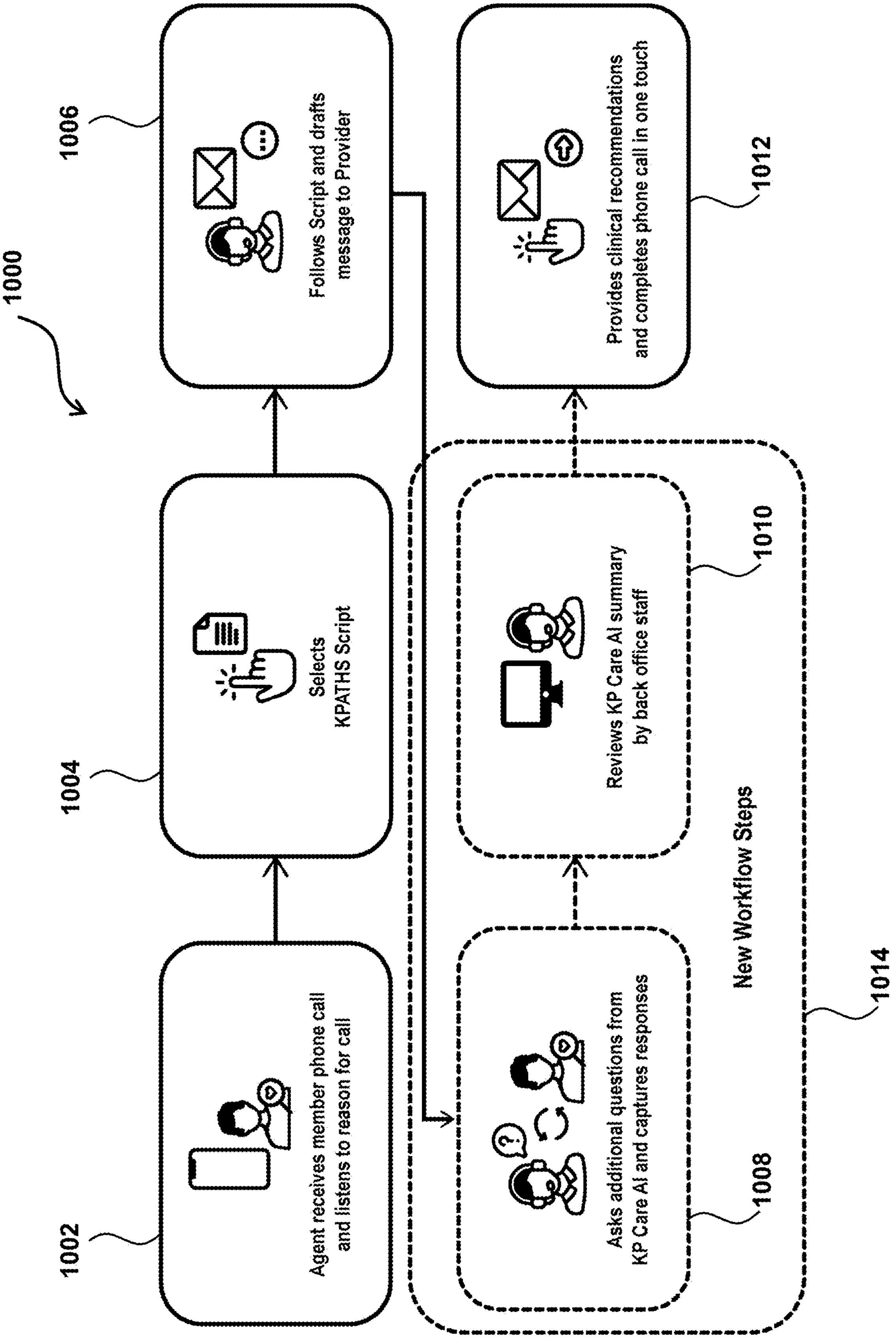
FIG. 10 is a flowchart showing an embodiment that may utilize the conversational interface to present recommendations that are refined through an iterative conversational process in accordance with embodiments of this disclosure.

FIG. 10 is a flowchart showing an embodiment of system 100 where routine 1000 may utilize the conversational interface 165 (FIG. 1) to initially present the clinician (e.g., medical professionals, their support staff, vendors, contract workers, patients, guardians, caregivers, third party systems) with broadly conceived recommendations that are refined through an iterative conversational process 1100 (FIG. 11) between the clinician and the conversational interface 165. The iterative conversational process 1100 may refer to an LLM chatbot that continues to elicit prompts from the clinician until the clinician is satisfied with the recommendation (e.g., feedback, decision support recommendations, prescription data, medication interactions, message severity response protocols, appointment recommendations) produced by the CDSS routine 1000 may be recognized as an example implementation of system 100 shown in FIG. 1. Here, Block 1002 represents the system server 110 receiving the clinical service request from the at least one clinical interface 135. Routine 1000 may include using the CDSS to employ the classification model to determine the message intent of the clinical service request and generate via the processor, an intermediary recommendation based on the at least one relevant clinical rule, the at least one primary workflow, a machine learning model, a message intent, and the plurality of semantic tokens (Block 1004). The intermediary recommendation may be a component, (e.g., a subroutine) of the generalized intermediary workflow that is used to provide the clinician with sufficient information to understand and begin to respond to the clinical service request. Routine 1000 may further include initiating the at least one primary workflow to transfer the intermediary recommendation to the clinician (Block 1006). Alternatively, Block 1006 may include routing the intermediary recommendation to the appropriate organizational processing subsystem 130 where any authorized recipient would interact with the conversational interface 165 as described herein. Routine 1000 may represent the conversational interface 165 as iterative process 1014 that includes prompting the clinician to enter data and information in response to the intermediary recommendation (Block 1008). The intermediary recommendation may include prompting the clinician (e.g., "What would you like to do?"). The clinician may then enter a general query (e.g., "How do I get to the nearest member hospital?") and the iterative conversational process may include returning the clinician's query to the CDSS to employ at least one of NLP, LLM analysis, clinical metadata ontology, the classification model, clinical knowledge, operational knowledge, and statistical analyses to determine a message or response intent. Block 1008 may further include providing the clinician with a decision support recommendation that includes a response (e.g., direction to the member hospital). The response in the decision support recommendation and the clinician's input may be used as feedback and training data to refine the CDSS. For example, a reward model may be used to generate training data that is fed into the classification model and facilitates identifying message intent. Further, the training data may be fed into the conversational interface 165 to generate recommendations. In some embodiments, the intent classification model, the clinical metadata ontology 140, the clinical rules engine, and the clinical workflow repository are updated based on the aforementioned feedback. For example, the updates may include retraining the classification model based on expert scoring of the decision support recommendation, an internal scoring and validation system, and clinician interaction with the system 100 (Block 1010). Routine 1000 may further include generating a summary of the clinician's interactions with the conversational interface 165 and feeding this entire summary into the machine learning model to further refine the system's 100 ability to produce accurate decision support recommendations (Block 1012). For example, a clinician's entire conversation with the chatbot may be summarized in Block 1012 and then entered into a patient's medical history to warn prescribers of newly identified problematic drug interactions for the patient.

In some embodiments, the iterative conversational process may execute a modified version of method 800 (FIG. 8) where the responses and prompts that the clinician supplies to the conversational interface 165 are processed similar to clinical service requests that are received from the at least one clinical interface 135. That is, the information entered into the at least one clinical interface 135 may be subjected to operations 801-806. However, the at least one decision support recommendation is routed back to the clinician rather than a different entity within the multi-tiered organizational structure 170 (FIG. 1).

Figure 11:
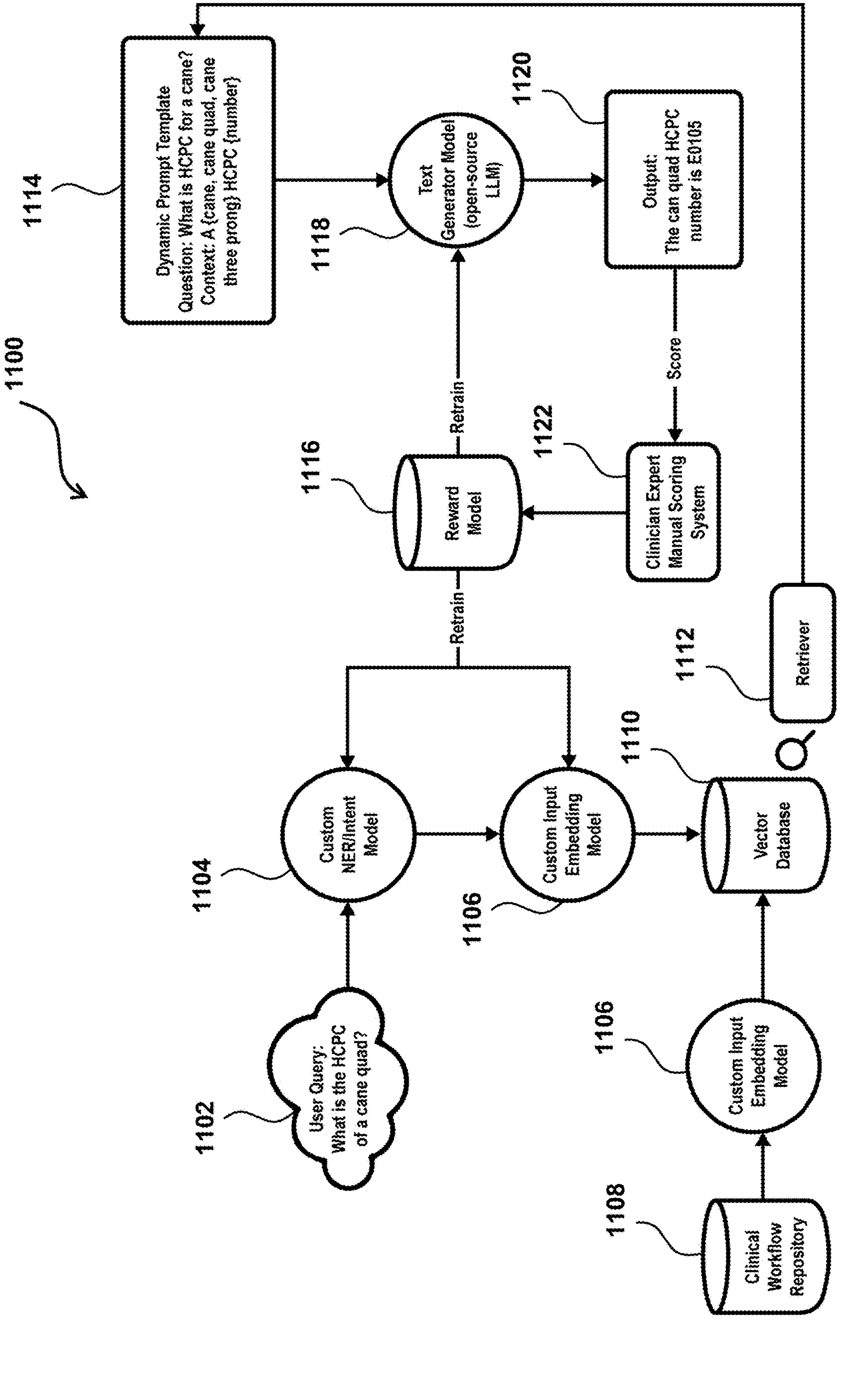
FIG. 11 is a block diagram that illustrates an iterative conversational process in accordance with embodiments of this disclosure.

FIG. 11 shows a block diagram or an iterative conversational process 1100 for transforming input 1102 (e.g., clinician prompts, clinical service requests, interaction data, data from external servers or sources, data stored in a database) received by the system server 110 into decision support recommendations. In some embodiments the classification model may include operation 1104. The output from a reward model 1116 is used as training data (e.g., through backpropagation) to update and refine features (e.g., the transformer layers, self-attention blocks, multilayer perceptrons, embedding matrices, SoftMax parameters and temperatures) of the classification model 1104. For example, input 1102 may be parsed into the plurality of semantic tokens, and organization-specific weights may be assigned to each of the plurality of semantic tokens during operation 1104. The organization-specific weights may be updated based on training data supplied by the reward model 1116. In some embodiments the results of operation 1104 (e.g., the clinical service request, the plurality of semantic tokens, weighting data) are supplied to a custom input embedding model 1106 to transform the clinical service request 1102 and the plurality of semantic tokens into a format optimized for and tailored to the specific medical service provider organization (e.g., multi-tiered organizational structure 170 as shown in FIG. 1). In some embodiments, the custom input embedding model 1106 may be a transformer (e.g., LoRA, QLoRA, MAMBA) that receives data (e.g., 1102, 1108) from external, and potentially disparate, sources and generates an organization-specific vectorized representation of the data. For example, the plurality of semantic tokens associated with a neonatal cardiologist may have unique weights that encode embeddings where frequently prescribed heart medications are in a similar space (e.g., semantically associated with) as patients under three-months old. Further, the format may be optimized for and tailored to the specific medical service provider organization through the inclusion of data 1108 supplied by the clinical workflow repository 150 and other components of the system 100 (e.g., the SCMO engine 140, the clinical rules engine 145, the communications interface 120, the database 125) (FIG. 1). In some embodiments, the conversational interface 165 (FIG. 1) retrains the custom input embedding model 1106 after each iteration of the iterative conversational process 1100 (FIG. 11).

Continuing with FIG. 11, the organization-specific vectorized representation of the input 1102 generated by the custom input embedding model 1106 may then be supplied to a vector database 1110 where it is correlated, via the processor 115 (FIG. 1), with a vectorized representation of data 1108 from the clinical workflow repository 150. For example, conversational interface 165 may generate a value vector from input 1102 that modifies the organization-specific vectorized representation of the intermediary workflow to incorporate patient-specific data (e.g., appointment information, medication interactions, age, location, dietary restrictions) included in input 1102. In some embodiments, the correlation may generate a dynamic prompt template 1114 for the intermediary recommendation. The dynamic prompt template 1114 may be a contextually rich tensor (e.g., a high dimensional vector including message intent, organization-specific weights, intermediary recommendations, at least one relevant clinical rule, primary workflow) that may include a prompt and at least one contextual token used by the chatbot text generator model 1118 to present the intermediary recommendation to the clinician during the iterative conversational process 1100. In some embodiments, retriever 1112 may be an operation that packages the relevant data from the vector database 1110 into the dynamic prompt template 1114.

In some embodiments, the text generator model 1118 may output the intermediary recommendation as a message that may conform to clinician-specific preferences to facilitate relaying data to the clinician (FIG. 11). That is, the iterative conversational process 1100 (FIG. 11) may include generating, via the processor, at least one natural language clinical decision support recommendation by inputting the dynamic prompt template 1114 into the text generator model 1118. For example, the input 1102 may be an unstructured text query seeking the product code for canes. One iteration of the iterative conversational process 1100 may determine that the clinician has an upcoming appointment with a patient who prefers quad canes and therefore infer that the clinician is looking for the product code for quad canes. Accordingly, the dynamic prompt template 1114 may include a query for canes and a set of contextual tokens that direct the text generator model 1118 to output an intermediary recommendation message 1120 with the product code for quad canes through the conversational interface 165. If the clinician is satisfied with the message 1120, they can end their interaction with the system 100. However, the clinician may enter subsequent related or unrelated prompts that may include structured and unstructured data. The subsequent prompts may become input 1102 for subsequent iterations of the iterative conversational process 1100 (FIG. 11). Further, the message 1120 may be scored for accuracy by at least one attention block 1122 (e.g., single-head attention blocks, multi-head attention blocks, self-attention heads, cross-attention heads) to produce weights, value vectors, and output matrices associated with more refined and contextually rich embeddings for subsequent iterations of the iterative conversational process 1100. In some embodiments, the iterative conversational process 1100 includes receiving, via the processor 115 (FIG. 1), scores for the at least one natural language clinical decision support recommendation from Clinical Subject Matter Experts as at least one attention head in the at least one attention block 1122 for the iterative conversational process 1100. In some embodiments, the at least one attention block 1122 may employ attention mechanisms aimed at making context windows scalable for large parameter sets (e.g., sparse attention mechanisms, blockwise attention, Linformer, Reformer, ring attention, Longformer, adaptive attention). The refined embeddings of the attention block 1122 may be supplied to the reward model 1116 to progressively embed contextual meaning from organization-specific context windows. In some embodiments, the iterative conversational process 1100 (FIG. 11) includes retraining, via the processor 115, the text generator model 1118, the custom input embedding model 1106, and the classification model 1104 based on the training data.

Figure 12:
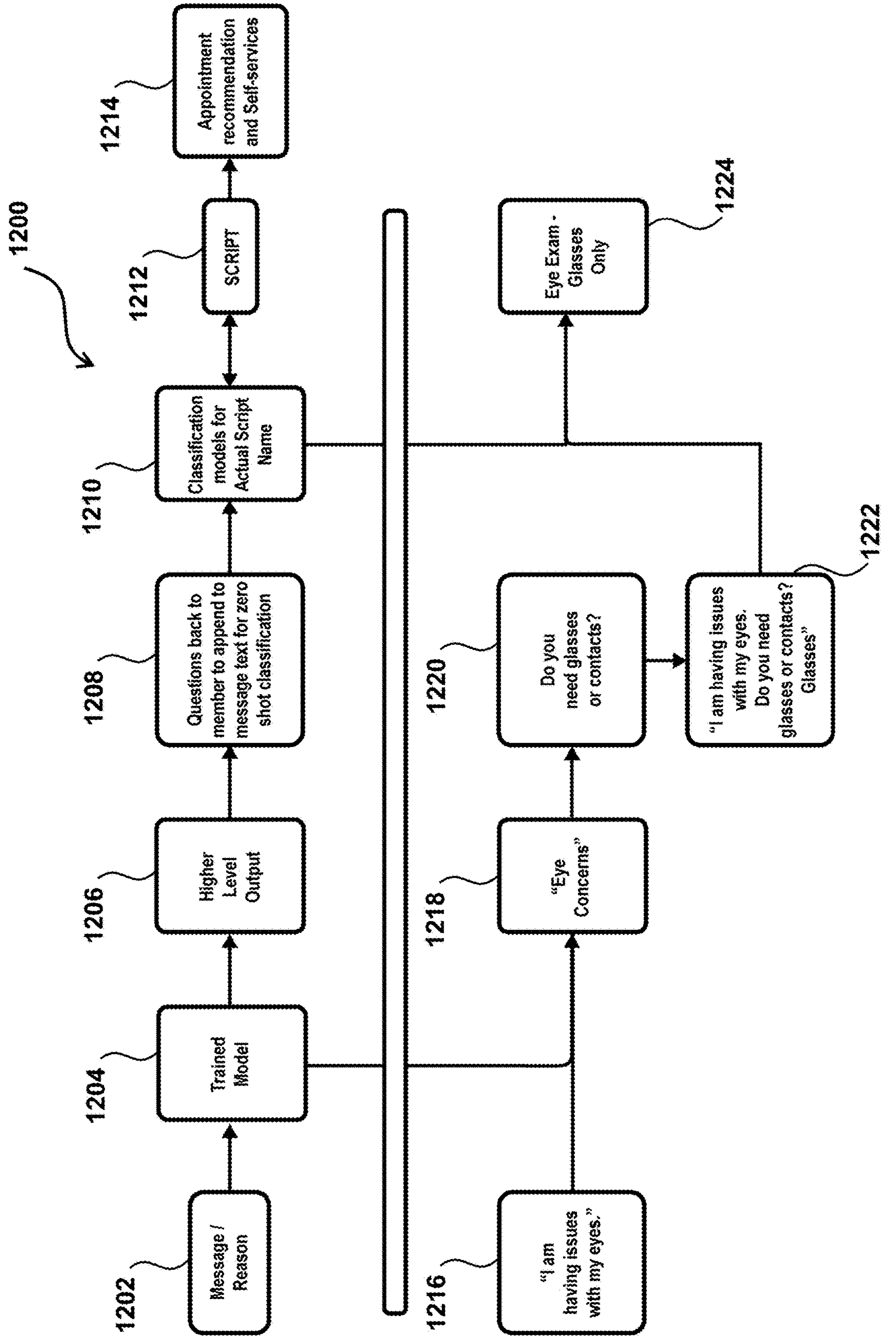
FIG. 12 is a block diagram that illustrates a process of fine-tuning the clinical support recommendation in accordance with embodiments of this disclosure.

FIG. 12 shows a flow chart for performing the preliminary triage operation 1200 to generate, via the processor 115 (FIG. 1), the intermediary recommendation based on the at least one relevant clinical rule, the at least one primary workflow, the machine learning model, message intent, and the plurality of semantic tokens. FIG. 12 further shows example prompts that may be generated by the clinician or the iterative conversational process 1100 (FIG. 11). In some embodiments, the intermediary recommendation is generated by the at least one primary workflow and the at least one relevant clinical rule acting as operators on data included in the at least one service request. Descriptions for FIG. 12 relate to updates, transformation, and other operations that refine the intermediary workflow and the at least one relevant clinical rule, during the iterative conversational process 1100. In block 1202, the clinical service request is received and parsed into the plurality of semantic tokens. For example, the clinical service request shown in block 1216 may be a statement indicating the patient is having eye trouble. The preliminary triage operation 1200 may include supplying the plurality of semantic tokens to trained model 1204 (e.g., classification model 1104) to generate a high-level output 1206 (e.g., the intermediary recommendation) 1206. The high level output 1206 may refer to the generalized representation of the content of the clinical service request (e.g., the message intent). For example, block 1218 illustrates the high level output 1206 of the trained model 1204 describing the clinical service request as relating to eye concerns. The preliminary triage operation 1200 may further include generating, via the processor 115 (FIG. 1), a refined recommendation (Block 1222) by performing the iterative conversational process 1100 (Block 1208).

In some embodiments, the iterative conversational process 1100 includes parsing, classifying, and identifying clinical content included in the interaction data. The clinical content may include information gathered during the iterative conversational process 1100 that serves to refine the custom input embedding model 1106 (FIG. 11) to provide accurate and useful decision support recommendations that generate the refined recommendation 1222. For example, the intermediary recommendation generated during Block 1208 may be a broad prompt (Block 1220) directing the clinician to ask if the patient needs glasses or contacts. This broad prompt may be determined based on the relevant tokens within an embedding space generated by the custom input embedding model 1106 (FIG. 11). The preliminary triage operation 1200, may include using the refined recommendation 1222 to identify at least one rule adapter in the clinical rules engine for each iteration of the iterative conversational process 1100. For example, the interaction data may include the clinician's response that the patient may require a more comprehensive eye exam than that suggested in the intermediary recommendation 1220. The at least one rule adapter may then embed the additional context of potential eye problems when refining the intermediary recommendation to generate the refined recommendation 1222 after an iteration of the iterative conversational process 1100. In some embodiments, the at least one rule adapter may serve as a fine-tuning function that modifies the at least one relevant clinical rule used to initialize the at least one primary workflow. For example, the iterative conversational process 1100 (FIG. 11) may include using the at least one intermediary workflow, the at least one rule adapter, the refined recommendation 1222, and the interaction data from each iteration of the iterative conversational process 1100 as training data for the machine learning model 200 of FIG. 2 (e.g., classification model 1104, custom input embedding model 1106, reward model 1116, and text generator model 1118 as shown in FIG. 11). The refined recommendation 1222 may be further refined through multiple iterations of the iterative conversational process 1100.

In some embodiments, the results of the iterative conversational process 1100 in block 1208 are compiled to generate the dynamic prompt template 1114 (FIG. 11) and transferred to block 1210 for the classification model 1104 to identify the message intent for the refined recommendation 1222.

In some embodiments, the clinical rules engine 145 (FIG. 1) may generate the at least one relevant clinical rule as a cumulative result of the at least one rule adapter identified during each iteration of the iterative conversational process 1100 (FIG. 11). For example, the iterative conversational process 1100 may generate a vectorized representation of the at least one relevant clinical rule that contains all relevant context generated through each iteration. In some embodiments, the iterative conversational process 1100 includes searching, via the processor 115 (FIG. 1), the clinical workflow repository 150 associated with the specific medical service provider organization (e.g., multi-tiered organizational structure 170 as shown in FIG. 1) to identify at least one intermediary workflow based on the clinical content and the at least one rule adapter. In some embodiments, the iterative conversational process 1100 includes using a plurality of subsidiary rule adapters to refine the at least one relevant clinical rule. The plurality of subsidiary adapters may be used to fine-tune the organization-specific embedding space.

In some embodiments the at least one intermediary workflow of the final iteration becomes the at least one primary workflow. Accordingly, the refined recommendation 1222 and the at least one primary workflow may be compiled to form a context-rich summary of the operations executed during the iterative conversational process 1100 (FIG. 11). For example, the preliminary triage operation 1200 may include generating, via the processor 115 (FIG. 1), an organization-specific summary 1212 by inputting data gathered during the iterative conversational process 1100 into a summarization model. In some embodiments, the organization-specific summary 1212 may be patient and/or organization specific and used to guide the patient down desired clinical booking pathways when sending and responding to clinical service requests. For example, the patient may be prompted to schedule an appointment at a new facility because their primary care provider now uses it as their home office.

Continuing descriptions of FIG. 12, In some embodiments, the summarization model may be an LLM capable of generating natural language reports. For example, the summarization model may generate a response 1224 to the clinical service request that includes sufficient information for the patient to perform self-service operations during block 1214. For example, the response may suggest the patient schedule an eye exam for glasses and not contact lenses using a self-service portal (e.g., clinical interface 135 (FIG. 1)). In some embodiments, the response 1224 is based on the refinements to the clinical service request developed during the iterative conversational process 1100. For example, the response 1224 may include clinician notes, prescriptions, treatment recommendations, appointment scheduling, and medical diagnosis. In some embodiments, the response 1224 may include an action plan that may be transmitted to an electronic health records (EHR) system for further review by clinical staff and subject matter experts. The action plan may be further refined to fit the organizational processing subsystem 130 in which the clinical staff interacting with the iterative conversational process 1100 operate.

Figure 13:
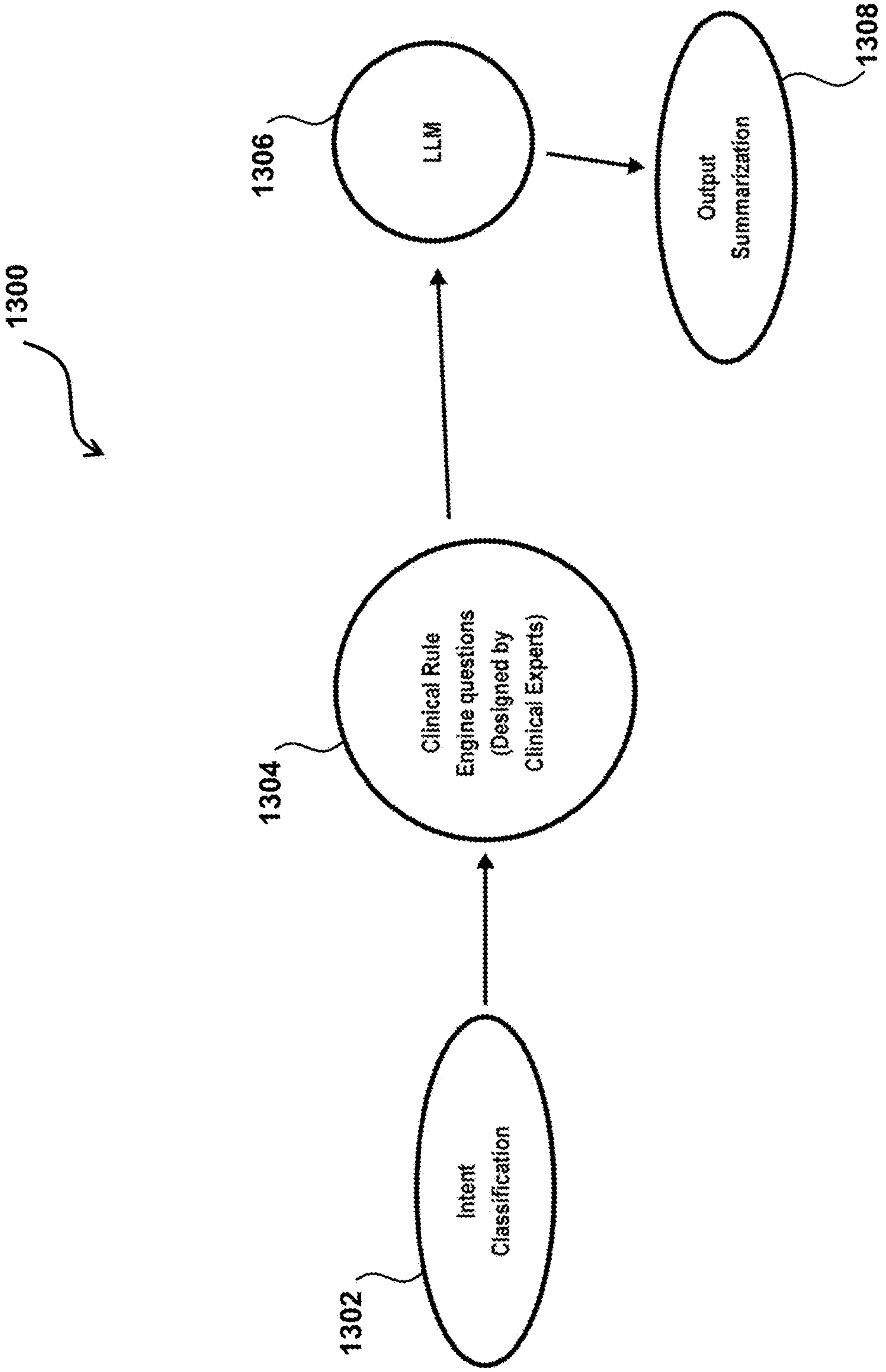
FIG. 13 is a block diagram that illustrates a process of transforming a clinical service request into a context-rich treatment summary in accordance with embodiments of this disclosure.

FIG. 13 shows a flowchart illustrating a routine 1300 for generating an organization-specific summarization from the clinical service request. The clinical service request may be subjected to an intent classification in operation 1302 to generate the intermediary recommendation. Once the message intent is identified operation 1304 begins by identifying the clinical rules and workflows for addressing the clinical service request. Routine 1300 may include a machine learning block 1306 that translates the output of 1304 into a natural language summary 1308.

Those skilled in the art will also appreciate that while various items are illustrated as being stored in memory or on storage while being used, these items or portions of them may be transferred between memory and other storage devices for purposes of memory management and data integrity. Alternatively, in other embodiments some or all of the software components may execute in memory on another device and communicate with the illustrated computer system via inter-computer communication. Some or all of the system components or data structures may also be stored (e.g., as instructions or structured data) on a computer-accessible medium or a portable article to be read by an appropriate drive, various examples of which are described above. In some embodiments, instructions stored on a computer-accessible medium separate from computer system 900 may be transmitted to computer system 900 via transmission media or signals such as electrical, electromagnetic, or digital signals, conveyed via a communication medium such as a network or a wireless link. Various embodiments may further include receiving, sending, or storing instructions or data implemented in accordance with the foregoing description upon a computer-accessible medium. Accordingly, the present invention may be practiced with other computer system configurations.

While the Figures show different operations for clinical decision support systems and steps that may be implemented according to a method and embodiments herein, the order of steps is not intended to be limited to the order as shown in the Figures, nor is the order of the Figures intended to imply sequential implementation of such steps and operations. It should be understood that such steps may be re-arranged, multiplied (e.g., duplicated and/or implemented more than once) as well as removed based on healthcare entity needs and/or patient preferences, for example. As used herein, "configured to [verb]" shall mean that the identified element or assembly has a structure that is shaped, sized, disposed, coupled, and/or configured to perform the identified verb. For example, a member that is "configured to move" is movably coupled to another element and includes elements that cause the member to move, or the member is otherwise configured to move in response to other elements or assemblies. As such, as used herein, "configured to [verb]" recites structure and not function. Further, as used herein, "configured to [verb]" means that the identified element or assembly is intended to, and is designed to, perform the identified verb. Thus, an element that is merely capable of performing the identified verb, but which is not intended to, and is not designed to, perform the identified verb is not "configured to [verb]."

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

The following list of embodiments describes various aspects of the systems and methods described herein, which may be combined in any combination.

Example Embodiment 1: A system for clinical decision support may include: a processor configured to: receive a clinical service request from at least one of an electronic health records system, a patient portal, a call center, a third-party system, and a professional referral; parse the clinical service request into a plurality of semantic tokens that includes clinical metadata for clinical metadata ontology using a machine learning model, clinical knowledge, operational knowledge, and statistical analyses; execute a preliminary triage operation with the plurality of semantic tokens to: classify and/or label the clinical service request, a classification and/or label configured to account for both a type of the clinical service request, and/or a varying severity and/or urgency of the clinical service request, and identify at least one relevant clinical rule and at least one primary workflow for responding to the clinical service request based on a classification and/or label, the at least one relevant clinical rule and the at least one primary workflow each being unique and tailored for a specific medical service provider organization; generate at least one decision support recommendation based on the at least one relevant clinical rule and the at least one primary workflow, where the at least one decision support recommendation includes recommendations for patient care that account for at least one of medication history, preexisting conditions, information gathered during a doctor visit, and medical data gathered from external sources; and transfer the at least one decision support recommendation to a multi-tiered organizational processing subsystem based on the at least one primary workflow, the multi-tiered organizational processing subsystem being unique and tailored for the specific medical service provider organization, where general clinical service requests are addressed by appropriately non-specialized or non-localized remedies found in a lowest tier of the organizational processing subsystem, and where specialized clinical service requests may be addressed by remedies found in a highest tier of the organizational processing subsystem, and where each tier of the organizational processing subsystem has a dedicated workflow for clinical service requests.

Example Embodiment 2: A method for clinical decision support may include: receiving, via a processor, a clinical service request; parsing, via the processor, the clinical service request into a plurality of semantic tokens; classifying and/or labeling, via the processor, the clinical service request, a classification and/or label configured to account for both a type of the clinical service request and/or a varying severity and/or urgency of the clinical service request; executing, via the processor, a preliminary triage operation with the plurality of semantic tokens to identify at least one relevant clinical rule and at least one primary workflow for responding to the clinical service request based on a classification and/or label, the at least one relevant clinical rule and the at least one primary workflow are each unique and tailored for a specific medical service provider organization; generating, via the processor, at least one decision support recommendation based on the at least one relevant clinical rule and the at least one primary workflow; and transferring, via the processor, the at least one decision support recommendation to an organizational processing subsystem for the specific medical service provider organization based on the at least one primary workflow.

Example Embodiment 3: The method of Example Embodiment 2, where parsing the clinical service request into the plurality of semantic tokens is: performed using a classification model, clinical knowledge, operational knowledge, and statistical analyses, is one such parsing among millions of other clinical service requests, and is based on prior parsing of millions of prior clinical service requests.

Example Embodiment 4: The method of Example Embodiment 2 or Example Clause 3, where classifying the clinical service request is: performed using the classification model, clinical knowledge, operational knowledge, and statistical analyses to determine a message intent; and executed to incorporate the clinical service request and the plurality of semantic tokens into a custom input embedding model, where the custom input embedding model transforms the clinical service request and the plurality of semantic tokens into a format optimized for and tailored to the specific medical service provider organization.

Example Embodiment 5: The method of any one of Example Embodiment 2-4, where the custom input embedding model acts as an intermediary transformer that generates organization-specific vectorized representations of data from disparate sources, the method further may include: correlating, via the processor, a vectorized representation of the clinical service request with a vectorized representation of a clinical workflow repository; generating, via the processor, a dynamic prompt template based on the correlating; generating, via the processor, at least one natural language clinical decision support recommendation by inputting the dynamic prompt template into a text generator model; receiving, via the processor, scores for the at least one natural language clinical decision support recommendation; and generating, via the processor, training data by inputting the scores into a reward model; retraining, via the processor, the text generator model, the custom input embedding model, and the classification model based on the training data.

Example Embodiment 6: The method of any one of Example Embodiment 2-5, where the plurality of semantic tokens includes clinical metadata for clinical metadata ontology, the clinical metadata ontology: describing clinical operations for the medical service provider organization; describing grouping structures for semantic tokens, and associated attributes; and may include domain specific descriptions based on specialties and a workflow associated with the medical service provider organization.

Example Embodiment 7: The method of any one of Example Embodiment 2-6, where the plurality of semantic tokens includes at least one associated with a type, a severity, an urgency, a service identifier, an intent, and clinical content of the clinical service request.

Example Embodiment 8: The method of any one of Example Embodiment 2-7, may include: reviewing, via the processor, the clinical content with a clinical rules engine to determine the at least one relevant clinical rule; and searching, via the processor, a clinical workflow repository associated with the specific medical service provider organization to identify the at least one primary workflow based on the clinical content and the at least one relevant clinical rule.

Example Embodiment 9: The method of any one of Example Embodiment 2-8, where the preliminary triage operation includes: generating, via the processor, a intermediary recommendation based on the at least one relevant clinical rule, the at least one primary workflow, a machine learning model, a message intent, and the plurality of semantic tokens; directing, via the processor, the organizational processing subsystem to prompt to interact with the intermediary recommendation; and receiving, via the processor, interaction data from the organizational processing subsystem.

Example Embodiment 10: The method of any one of Example Embodiment 2-9, where the preliminary triage operation functions as a chatbot interface for performing interactive advising and clinical decision support.

Example Embodiment 11: The method of any one of Example Embodiment 2-10, where the preliminary triage operation includes generating, via the processor, a refined recommendation by performing an iterative conversational process, and where the iterative conversational process includes parsing, classifying, and identifying clinical content included in the interaction data; and where the refined recommendation is used to identify at least one rule adapter in the clinical rules engine for each iteration of the iterative conversational process, and where the clinical rules engine generates the at least one relevant clinical rule as a cumulative result of the at least one rule adapter identified during each iteration of the iterative conversational process.

Example Embodiment 12: The method of any one of Example Embodiment 2-11, where the iterative conversational process includes searching, via the processor, the clinical workflow repository associated with the specific medical service provider organization to identify at least one intermediary workflow based on the clinical content and the at least one rule adapter, and where the at least one intermediary workflow of the final iteration becomes the at least one primary workflow.

Example Embodiment 13: The method of any one of Example Embodiment 2-12, where the iterative conversational process includes using the at least one intermediary workflow, the at least one rule adapter, the refined recommendation, and the interaction data from each iteration of the iterative conversational process as training data for the machine learning model.

Example Embodiment 14: The method of any one of Example Embodiment 2-13, where the preliminary triage operation includes generating, via the processor, an organization-specific summary by inputting data gathered during the iterative conversational process into a summarization model, and where the organization-specific summary is associated with the at least one decision support recommendation.

Example Embodiment 15: The method of any one of Example Embodiment 2-14, where the summarization model is a large language model.

Example Embodiment 16: The method of any one of Example Embodiment 2-15, where the iterative conversational process includes using a plurality of subsidiary rule adapters to refine the at least one relevant clinical rule.

Example Embodiment 17: The method of any one of Example Embodiment 2-16, where at least one machine learning model is used to implement the parsing, reviewing with the clinical rules engine, and searching of the clinical workflow repository to enable improved semantic tokenization, and workflow selection.

Example Embodiment 18: The method of any one of Example Embodiment 2-17, where the service identifier is included as criteria in the search to identify the at least one primary workflow, and where the service identifier denotes at least one of an appointment request, a medication refill request, referral questions, lab test results, imaging results, a symptom question, a procedure question, a form request, an immunization question, an obesity medicine question, a personal health information update, and an indication of where a patient or a patient's proxy is in a medical service progression.

Example Embodiment 19: The method of any one of Example Embodiment 2-18, where a plurality of organizational processing subsystems is arranged into a multi-tiered response hierarchy, where the multi-tiered organizational processing subsystem is unique and tailored for the specific medical service provider organization, where a lowest tier of the response hierarchy responds to clinical service requests denoted by service identifiers directed toward satisfying general service requests, and where each tier in a plurality of subsequent tiers of the organizational processing subsystem is directed to an increasingly specialized group of possible respondents.

Example Embodiment 20: The method of any one of Example Embodiment 2-19, where the multi-tiered organizational processing subsystem is configured to process clinical service requests, depending on how various respondents or groups of respondents associated with the multi-tiered organizational processing subsystem are defined, in a hierarchical manner, in a direct manner skipping one or more tiers of the multi-tiered organizational processing subsystem depending on the nature of a clinical service request, in an intra-tier transfer manner between multiple respondents within the same tier level, and/or in a dynamic manner up and/or down the multi-tiered organizational processing subsystem depending on a medical service progression for the clinical service request.

Example Embodiment 21: The method of any one of Example Embodiment 2-20, where the multi-tiered organizational processing subsystem is managed by multiple providers with different scopes of practice that are defined by local and/or state regulation.

Example Embodiment 22: The method of any one of Example Embodiment 2-21, where the decision support recommendation is transferred directly into an individual's mailbox for processing at a highest tier of the multi-tiered organizational processing subsystem.

Example Embodiment 23: The method of any one of Example Embodiment 2-22, where the decision support recommendation is transferred to a regional hub for processing at the lowest tier of the multi-tiered organizational processing subsystem.

Example Embodiment 24: The method of any one of Example Embodiment 2-23, where the decision support recommendation is transferred to a processing pool for at least one intermediary tier of the multi-tiered organizational processing subsystem, and where the processing pool may include a pharmacy pool, a prescriber pool, a receptionist pool, a medical assistant and/or vocational nurse pool, an administrative pool, a form pool, a local medical service pool, a subspecialty pool, and/or a behavioral health pool.

Example Embodiment 25: The method of any one of Example Embodiment 2-24, where the clinical service request is received from at least one of an electronic health records system, a patient portal, a call center, a third-party system, and a professional referral.

Example Embodiment 26: The method of any one of Example Embodiment 2-25, further where an operational dashboard is configured to track outputs associated with clinical service requests, and where the operational dashboard is configured to update minute by minute, hourly, shift by shift, daily, weekly, and/or monthly to facilitate resource allocation by the medical service provider organization.

Example Embodiment 27: A software based computing system for clinical decision support may include a non-transitory computer-readable medium storing instructions configured to cause the computing system to: receive a clinical service request; parse the clinical service request into a plurality of semantic tokens; classify and/or label the clinical service request, a classification and/or label configured to account for both a type of the clinical service request and/or a varying severity and/or urgency of the clinical service request; execute a preliminary triage operation with the plurality of semantic tokens to identify at least one relevant clinical rule and at least one primary workflow for responding to the clinical service request based on a classification and/or label, the at least one relevant clinical rule and the at least one primary workflow are each unique and tailored for a specific medical service provider organization; generate at least one decision support recommendation based on the at least one relevant clinical rule and the at least one primary workflow; and transfer the at least one decision support recommendation to an organizational processing subsystem for the specific medical service provider organization based on the at least one primary workflow.

Example Embodiment 28: The system of Example Embodiment 27, where parsing the clinical service request into the plurality of semantic tokens is: performed using a machine learning model, clinical knowledge, operational knowledge, and statistical analyses; is one such parsing among millions of other clinical service requests; and is based on prior parsing of millions of prior clinical service requests.

Example Embodiment 29: The system of Example Embodiment 27 or Example Clause 28, where classifying the clinical service request is: performed using a classification model, clinical knowledge, operational knowledge, and statistical analyses to determine a message intent; and executed to incorporate the clinical service request and the plurality of semantic tokens into a custom input embedding model, where the custom input embedding model transforms the clinical service request and the plurality of semantic tokens into a format optimized for and tailored to the specific medical service provider organization.

Example Embodiment 30: The system of any one of Example Embodiment 27-29, where the custom input embedding model acts as an intermediary transformer that generates organization-specific vectorized representations of data from disparate sources, the instructions further causing the computing system to: correlate a vectorized representation of the clinical service request to a vectorized representation of a clinical workflow repository; generate a dynamic prompt template based on the correlating; generate at least one natural language clinical decision support recommendation by inputting the dynamic prompt template into a text generator model; receive scores for the at least one natural language clinical decision support recommendation; generate training data by inputting the scores into a reward model; and retrain the text generator model, the custom input embedding model, and the classification model based on the training data.

Example Embodiment 31: The system of any one of Example Embodiment 27-30, where the plurality of semantic tokens includes clinical metadata for clinical metadata ontology, the clinical metadata ontology: describing clinical operations for the medical service provider organization; describing grouping structures for semantic tokens, and associated attributes; and may include domain specific descriptions based on specialties and a workflow associated with the medical service provider organization.

Example Embodiment 32: The system of any one of Example Embodiment 27-31, where the plurality of semantic tokens includes at least one associated with a type, a severity, an urgency, a service identifier, an intent, and clinical content of the clinical service request.

Example Embodiment 33: The system of any one of Example Embodiment 27-32, where the instructions further cause the computing system to: review the clinical content with a clinical rules engine to determine the at least one relevant clinical rule; and search a clinical workflow repository associated with the specific medical service provider organization to identify the at least one primary workflow based on the clinical content and the at least one relevant clinical rule.

Example Embodiment 34: The system of any one of Example Embodiment 27-33, where the preliminary triage operation includes: generating an initial recommendation based on the at least one relevant clinical rule, the at least one primary workflow, a machine learning model, a message intent, and the plurality of semantic tokens; directing the organizational processing subsystem to prompt to interact with the initial recommendation; and receiving interaction data from the organizational processing subsystem.

Example Embodiment 35: The system of any one of Example Embodiment 27-34, where the preliminary triage operation functions as a chatbot interface for performing interactive advising and clinical decision support.

Example Embodiment 36: The system of any one of Example Embodiment 27-35, where the preliminary triage operation includes generating a refined recommendation by performing an iterative conversational process, the iterative conversational process includes parsing, classifying, and identifying clinical content included in the interaction data; and where the refined recommendation is used to identify at least one rule adapter in the clinical rules engine for each iteration of the iterative conversational process, and where the clinical rules engine generates the relevant clinical rule as a cumulative result of the at least one rule adapter identified during each iteration of the iterative conversational process.

Example Embodiment 37: The system of any one of Example Embodiment 27-36, where the iterative conversational process includes searching the clinical workflow repository associated with the specific medical service provider organization to identify at least one intermediary workflow based on the clinical content and the at least one rule adapter, and the at least one intermediary workflow of the final iteration becomes the at least one primary workflow.

Example Embodiment 38: The system of any one of Example Embodiment 27-37, where the iterative conversational process includes using a plurality of subsidiary rule adapters to refine the at least one relevant clinical rule.

Example Embodiment 39: The system of any one of Example Embodiment 27-38, where the iterative conversational process includes using the at least one intermediary workflow, the at least one rule adapter, the refined recommendation, and the interaction data from each iteration of the iterative conversational process as training data for the machine learning model.

Example Embodiment 40: The system of any one of Example Embodiment 27-39, where the preliminary triage operation includes generating an organization-specific summary by inputting data gathered during the iterative conversational process into a summarization model, and where the organization-specific summary is associated with the at least one decision support recommendation.

Example Embodiment 41: The system of any one of Example Embodiment 27-40, where the summarization model is a large language model.

Example Embodiment 42: The system of any one of Example Embodiment 27-41, where at least one machine learning model is used to implement the parsing, reviewing with the clinical rules engine, and searching of the clinical workflow repository to enable improved semantic tokenization, and workflow selection.

Example Embodiment 43: The system of any one of Example Embodiment 27-42, where the service identifier is included as criteria in the search to identify the at least one primary workflow, and the service identifier denotes at least one of an appointment request, a medication refill request, referral questions, lab test results, imaging results, a symptom question, a procedure question, a form request, an immunization question, an obesity medicine question, a personal health information update, and an indication of where a patient or a patient's proxy is in a medical service progression.

Example Embodiment 44: The system of any one of Example Embodiment 27-43, where a plurality of organizational processing subsystems is arranged into a multi-tiered response hierarchy, the multi-tiered organizational processing subsystem is unique and tailored for the specific medical service provider organization, a lowest tier of the response hierarchy responds to clinical service requests denoted by service identifiers directed toward satisfying general service requests, and each tier in a plurality of subsequent tiers of the organizational processing subsystem is directed to an increasingly specialized group of possible respondents.

Example Embodiment 45: The system of any one of Example Embodiment 27-44, where the multi-tiered organizational processing subsystem is configured to process clinical service requests, depending on how various respondents or groups of respondents associated with the multi-tiered organizational processing subsystem are defined, in a hierarchical manner, in a direct manner skipping one or more tiers of the multi-tiered organizational processing subsystem depending on the nature of a clinical service request, in an intra-tier transfer manner between multiple respondents within the same tier level, and/or in a dynamic manner up and/or down the multi-tiered organizational processing subsystem depending on a medical service progression for the clinical service request.

Example Embodiment 46: The system of any one of Example Embodiment 27-45, where the multi-tiered organizational processing subsystem is managed by multiple providers with different scopes of practice that are defined by local and/or state regulation.

Example Embodiment 47: The system of any one of Example Embodiment 27-46, where the decision support recommendation is transferred directly into an individual's mailbox for processing at a highest tier of the multi-tiered organizational processing subsystem.

Example Embodiment 48: The system of any one of Example Embodiment 27-47, where the decision support recommendation is transferred to a regional hub for processing at the lowest tier of the multi-tiered organizational processing subsystem.

Example Embodiment 49: The system of any one of Example Embodiment 27-48, where the decision support recommendation is transferred to a processing pool for at least one intermediary tier of the multi-tiered organizational processing subsystem, and the processing pool may include a pharmacy pool, a prescriber pool, a receptionist pool, a medical assistant and/or vocational nurse pool, an administrative pool, a form pool, a local medical service pool, a subspecialty pool, and/or a behavioral health pool.

Example Embodiment 50: The system of any one of Example Embodiment 27-49, where the clinical service request is received from at least one of an electronic health records system, a patient portal, a call center, a third-party system, and a professional referral.

Example Embodiment 51: The system of any one of Example Embodiment 27-50, where the one or more instructions further cause the device to: further where an operational dashboard is configured to track outputs associated with clinical service requests, and where the operational dashboard is configured to update minute by minute, hourly, shift by shift, daily, weekly, and/or monthly to facilitate resource allocation by the medical service provider organization.

What is claimed is:

1. A system for clinical decision support comprising:

a processor configured to:

receive a clinical service request from at least one of an electronic health records system, a patient portal, a call center, a third-party system, and a professional referral;

parse the clinical service request into a plurality of semantic tokens that includes clinical metadata for clinical metadata ontology using a machine learning model, clinical knowledge, operational knowledge, and statistical analyses;

transform the clinical service request into a vectorized representation using the machine learning model, the machine learning model including a custom input embedding model configured to transform the clinical service request and the plurality of semantic tokens into the vectorized representation, wherein the vectorized representation is organization-specific and optimized for a specific medical service provider organization, the vectorized representation being stored in a vector database that receives input via transformed data associated with each clinical service request, the plurality of semantic tokens, and from a clinical workflow repository associated with the specific medical service provider organization;

execute a preliminary triage operation with the plurality of semantic tokens to:

classify and/or label the clinical service request, a classification and/or label configured to account for both a type of the clinical service request, and/or a varying severity and/or urgency of the clinical service request, and identify at least one relevant clinical rule and at least one primary workflow for responding to the clinical service request based on a classification and/or label, the at least one relevant clinical rule and the at least one primary workflow each being unique and tailored for the specific medical service provider organization;

generate output, using a text generator model, comprising at least one decision support recommendation based on the vectorized representation, the at least one relevant clinical rule, and the at least one primary workflow, wherein the processor is further configured to correlate the vectorized representation of the clinical service request with a vectorized representation of the clinical workflow repository and to generate a dynamic prompt template based on the correlating, the dynamic prompt template being input into the text generator model to generate the at least one decision support recommendation, wherein the at least one decision support recommendation includes recommendations for patient care that account for at least one of medication history, preexisting conditions, information gathered during a doctor visit, and medical data gathered from external sources;

generate training data based on the generated output including the at least one decision support recommendation from the text generator model and at least one of: scoring, clinician input, validation, and feedback data, to refine the classification and/or label;

train or retrain the machine learning model using the generated training data; and transfer the at least one decision support recommendation to an organizational processing subsystem based on the at least one primary workflow, the organizational processing subsystem being unique and tailored for the specific medical service provider organization, wherein general clinical service requests are addressed by appropriately non-specialized or non-localized remedies found in a lowest tier of the organizational processing subsystem, and wherein specialized clinical service requests may be addressed by remedies found in a highest tier of the organizational processing subsystem, and wherein each tier of the organizational processing subsystem has a dedicated workflow for clinical service requests.

2. A method for clinical decision support comprising:

receiving, via a processor, a clinical service request;

parsing, via the processor, the clinical service request into a plurality of semantic tokens;

transforming, via the processor, the clinical service request into a vectorized representation using a machine learning model, the machine learning model including a custom input embedding model configured to transform the clinical service request and the plurality of semantic tokens into the vectorized representation, wherein the vectorized representation is organization-specific and optimized for the specific medical service provider organization, the vectorized representation being stored in a vector database that receives input via transformed data associated with each clinical service request, the plurality of semantic tokens, and from a clinical workflow repository associated with the specific medical service provider organization;

classifying and/or labeling, via the processor, the clinical service request, a classification and/or label configured to account for both a type of the clinical service request and/or a varying severity and/or urgency of the clinical service request;

executing, via the processor, a preliminary triage operation with the plurality of semantic tokens to identify at least one relevant clinical rule and at least one primary workflow for responding to the clinical service request based on a classification and/or label, the at least one relevant clinical rule and the at least one primary workflow are each unique and tailored for a specific medical service provider organization;

correlating, via the processor, the vectorized representation of the clinical service request with a vectorized representation of the clinical workflow repository;

generating, via the processor, a dynamic prompt template based on the correlating;

generating, via the processor and a text generator model, at least one decision support recommendation by inputting the dynamic prompt template into the text generator model, the at least one decision support recommendation being based on the vectorized representation, the at least one relevant clinical rule, and the at least one primary workflow;

generating training data based on the at least one decision support recommendation and at least one of: scoring, clinician input, validation, and feedback data, to refine the classification and/or label;

training or retraining the machine learning model using the generated training data; and transferring, via the processor, the at least one decision support recommendation to an organizational processing subsystem for the specific medical service provider organization based on the at least one primary workflow.

3. The method of claim 2, wherein parsing the clinical service request into the plurality of semantic tokens is:

performed using a classification model, clinical knowledge, operational knowledge, and statistical analyses, is one such parsing among millions of other clinical service requests, and is based on prior parsing of millions of prior clinical service requests.

4. The method of claim 2, wherein classifying the clinical service request is:

performed using a classification model, clinical knowledge, operational knowledge, and statistical analyses to determine a message intent; and executed to incorporate the clinical service request and the plurality of semantic tokens into the custom input embedding model, wherein the custom input embedding model transforms the clinical service request and the plurality of semantic tokens into the vectorized representation that is organization-specific and optimized for the specific medical service provider organization.

5. The method of claim 4, wherein the custom input embedding model acts as an intermediary transformer that generates organization-specific vectorized representations of data from disparate sources, the method further comprising:

generating, via the processor, at least one natural language clinical decision support recommendation by inputting the dynamic prompt template into the text generator model;

receiving, via the processor, scores for the at least one natural language clinical decision support recommendation; and generating, via the processor, training data by inputting the scores into a reward model;

retraining, via the processor, the text generator model, the custom input embedding model, and the classification model based on the training data.

6. The method of claim 2, wherein the plurality of semantic tokens includes clinical metadata for clinical metadata ontology, the clinical metadata ontology:

describing clinical operations for the medical service provider organization;

describing grouping structures for semantic tokens, and associated attributes; and comprising domain specific descriptions based on specialties and a workflow associated with the medical service provider organization.

7. The method of claim 6, wherein the plurality of semantic tokens includes at least one associated with a type, a severity, an urgency, a service identifier, an intent, and clinical content of the clinical service request.

8. The method of claim 7, comprising:

reviewing, via the processor, the clinical content with a clinical rules engine to determine the at least one relevant clinical rule; and searching, via the processor, a clinical workflow repository associated with the specific medical service provider organization to identify the at least one primary workflow based on the clinical content and the at least one relevant clinical rule.

9. The method of claim 8, wherein the preliminary triage operation includes:

generating, via the processor, an intermediary recommendation based on the at least one relevant clinical rule, the at least one primary workflow, a machine learning model, a message intent, and the plurality of semantic tokens;

directing, via the processor, the organizational processing subsystem to prompt to interact with the intermediary recommendation; and receiving, via the processor, interaction data from the organizational processing subsystem.

10. The method of claim 9, wherein the preliminary triage operation functions as a chatbot interface for performing interactive advising and clinical decision support.

11. The method of claim 9, wherein the preliminary triage operation includes generating, via the processor, a refined recommendation by performing an iterative conversational process, and wherein the iterative conversational process includes parsing, classifying, and identifying clinical content included in the interaction data; and wherein the refined recommendation is used to identify at least one rule adapter in the clinical rules engine for each iteration of the iterative conversational process, and wherein the clinical rules engine generates the at least one relevant clinical rule as a cumulative result of the at least one rule adapter identified during each iteration of the iterative conversational process.

12. The method of claim 11, wherein the iterative conversational process includes searching, via the processor, the clinical workflow repository associated with the specific medical service provider organization to identify at least one intermediary workflow based on the clinical content and the at least one rule adapter, and wherein the at least one intermediary workflow of the final iteration becomes the at least one primary workflow.

13. The method of claim 11, wherein the iterative conversational process includes using the at least one intermediary workflow, the at least one rule adapter, the refined recommendation, and the interaction data from each iteration of the iterative conversational process as training data for the machine learning model.

14. The method of claim 11, wherein the preliminary triage operation includes generating, via the processor, an organization-specific summary by inputting data gathered during the iterative conversational process into a summarization model, and wherein the organization-specific summary is associated with the at least one decision support recommendation.

15. The method of claim 14, wherein the summarization model is a large language model.

16. The method of claim 11, wherein the iterative conversational process includes using a plurality of subsidiary rule adapters to refine the at least one relevant clinical rule.

17. The method of claim 7, wherein at least one machine learning model is used to implement the parsing, reviewing with the clinical rules engine, and searching of the clinical workflow repository to enable improved semantic tokenization, and workflow selection.

18. The method of claim 17, wherein the service identifier is included as criteria in the search to identify the at least one primary workflow, and wherein the service identifier denotes at least one of an appointment request, a medication refill request, referral questions, lab test results, imaging results, a symptom question, a procedure question, a form request, an immunization question, an obesity medicine question, a personal health information update, and an indication of where a patient or a patient's proxy is in a medical service progression.

19. The method of claim 2, wherein a plurality of organizational processing subsystems is arranged into a multi-tiered response hierarchy, wherein the multi-tiered organizational processing subsystem is unique and tailored for the specific medical service provider organization, wherein a lowest tier of the response hierarchy responds to clinical service requests denoted by service identifiers directed toward satisfying general service requests, and wherein each tier in a plurality of subsequent tiers of the organizational processing subsystem is directed to an increasingly specialized group of possible respondents.

20. The method of claim 19, wherein the multi-tiered organizational processing subsystem is configured to process clinical service requests, depending on how various respondents or groups of respondents associated with the multi-tiered organizational processing subsystem are defined, in a hierarchical manner, in a direct manner skipping one or more tiers of the multi-tiered organizational processing subsystem depending on the nature of a clinical service request, in an intra-tier transfer manner between multiple respondents within the same tier level, and/or in a dynamic manner up and/or down the multi-tiered organizational processing subsystem depending on a medical service progression for the clinical service request.

21. The method of claim 19, wherein the multi-tiered organizational processing subsystem is managed by multiple providers with different scopes of practice that are defined by local and/or state regulation.

22. The method of claim 19, wherein the decision support recommendation is transferred directly into an individual's mailbox for processing at a highest tier of the multi-tiered organizational processing subsystem.

23. The method of claim 19, wherein the decision support recommendation is transferred to a regional hub for processing at the lowest tier of the multi-tiered organizational processing subsystem.

24. The method of claim 19, wherein the decision support recommendation is transferred to a processing pool for at least one intermediary tier of the multi-tiered organizational processing subsystem, and wherein the processing pool may include a pharmacy pool, a prescriber pool, a receptionist pool, a medical assistant and/or vocational nurse pool, an administrative pool, a form pool, a local medical service pool, a subspecialty pool, and/or a behavioral health pool.

25. The method of claim 2, wherein the clinical service request is received from at least one of an electronic health records system, a patient portal, a call center, a third-party system, and a professional referral.

26. The method of claim 2, further wherein an operational dashboard is configured to track outputs associated with clinical service requests, and wherein the operational dashboard is configured to update minute by minute, hourly, shift by shift, daily, weekly, and/or monthly to facilitate resource allocation by the medical service provider organization.

27. A software based computing system for clinical decision support comprising a non-transitory computer-readable medium storing instructions configured to cause the computing system to:

receive a clinical service request;

parse the clinical service request into a plurality of semantic tokens;

transform the clinical service request into a vectorized representation using a trained machine learning model, the trained machine learning model including a custom input embedding model configured to transform the clinical service request and the plurality of semantic tokens into the vectorized representation, wherein the vectorized representation is organization-specific and optimized for a specific medical service provider organization;

classify and/or label the clinical service request, a classification and/or label configured to account for both a type of the clinical service request and/or a varying severity and/or urgency of the clinical service request;

execute a preliminary triage operation with the plurality of semantic tokens to identify at least one relevant clinical rule and at least one primary workflow for responding to the clinical service request based on a classification and/or label, the at least one relevant clinical rule and the at least one primary workflow are each unique and tailored for the specific medical service provider organization;

generate at least one decision support recommendation based on the vectorized representation, at least one relevant clinical rule, and the at least one primary workflow, wherein the instructions are further configured to cause the computing system to correlate the vectorized representation of the clinical service request with a vectorized representation of a clinical workflow repository and to generate a dynamic prompt template based on the correlating, the dynamic prompt template being used to generate the at least one decision support recommendation;

generate training data based on the at least one decision support recommendation and at least one of: scoring, clinician input, validation, and feedback data, to refine the classification and/or label;

retrain the machine learning model using the generated training data; and transfer the at least one decision support recommendation to an organizational processing subsystem for the specific medical service provider organization based on the at least one primary workflow.

28. The system of claim 27, wherein parsing the clinical service request into the plurality of semantic tokens is:

performed using a machine learning model, clinical knowledge, operational knowledge, and statistical analyses;

is one such parsing among millions of other clinical service requests; and is based on prior parsing of millions of prior clinical service requests.

29. The system of claim 27, wherein classifying the clinical service request is:

performed using a classification model, clinical knowledge, operational knowledge, and statistical analyses to determine a message intent; and executed to incorporate the clinical service request and the plurality of semantic tokens into a custom input embedding model, wherein the custom input embedding model transforms the clinical service request and the plurality of semantic tokens into a format optimized for and tailored to the specific medical service provider organization.

30. The system of claim 29, wherein the custom input embedding model acts as an intermediary transformer that generates organization-specific vectorized representations of data from disparate sources, the instructions further causing the computing system to:

generate at least one natural language clinical decision support recommendation by inputting the dynamic prompt template into a text generator model;

receive scores for the at least one natural language clinical decision support recommendation;

generate training data by inputting the scores into a reward model; and retrain the text generator model, the custom input embedding model, and the classification model based on the training data.

31. The system of claim 27, wherein the plurality of semantic tokens includes clinical metadata for clinical metadata ontology, the clinical metadata ontology:

describing clinical operations for the medical service provider organization;

describing grouping structures for semantic tokens, and associated attributes; and comprising domain specific descriptions based on specialties and a workflow associated with the medical service provider organization.

32. The system of claim 31, wherein the plurality of semantic tokens includes at least one associated with a type, a severity, an urgency, a service identifier, an intent, and clinical content of the clinical service request.

33. The system of claim 32, wherein the instructions further cause the computing system to:

review the clinical content with a clinical rules engine to determine the at least one relevant clinical rule; and search a clinical workflow repository associated with the specific medical service provider organization to identify the at least one primary workflow based on the clinical content and the at least one relevant clinical rule.

34. The system of claim 33, wherein the preliminary triage operation includes:

generating an initial recommendation based on the at least one relevant clinical rule, the at least one primary workflow, a machine learning model, a message intent, and the plurality of semantic tokens;

directing the organizational processing subsystem to prompt to interact with the initial recommendation; and receiving interaction data from the organizational processing subsystem.

35. The system of claim 34, wherein the preliminary triage operation functions as a chatbot interface for performing interactive advising and clinical decision support.

36. The system of claim 34, wherein the preliminary triage operation includes generating a refined recommendation by performing an iterative conversational process, the iterative conversational process includes parsing, classifying, and identifying clinical content included in the interaction data; and wherein the refined recommendation is used to identify at least one rule adapter in the clinical rules engine for each iteration of the iterative conversational process, and wherein the clinical rules engine generates the relevant clinical rule as a cumulative result of the at least one rule adapter identified during each iteration of the iterative conversational process.

37. The system of claim 36, wherein the iterative conversational process includes searching the clinical workflow repository associated with the specific medical service provider organization to identify at least one intermediary workflow based on the clinical content and the at least one rule adapter, and the at least one intermediary workflow of the final iteration becomes the at least one primary workflow.

38. The system of claim 36, wherein the iterative conversational process includes using the at least one intermediary workflow, the at least one rule adapter, the refined recommendation, and the interaction data from each iteration of the iterative conversational process as training data for the machine learning model.

39. The system of claim 36, wherein the preliminary triage operation includes generating an organization-specific summary by inputting data gathered during the iterative conversational process into a summarization model, and wherein the organization-specific summary is associated with the at least one decision support recommendation.

40. The system of claim 39, wherein the summarization model is a large language model.

41. The system of claim 37, wherein the iterative conversational process includes using a plurality of subsidiary rule adapters to refine the at least one relevant clinical rule.

42. The system of claim 32, wherein at least one machine learning model is used to implement the parsing, reviewing with the clinical rules engine, and searching of the clinical workflow repository to enable improved semantic tokenization, and workflow selection.

43. The system of claim 42, wherein the service identifier is included as criteria in the search to identify the at least one primary workflow, and the service identifier denotes at least one of an appointment request, a medication refill request, referral questions, lab test results, imaging results, a symptom question, a procedure question, a form request, an immunization question, an obesity medicine question, a personal health information update, and an indication of where a patient or a patient's proxy is in a medical service progression.

44. The system of claim 27, wherein a plurality of organizational processing subsystems is arranged into a multi-tiered response hierarchy, the multi-tiered organizational processing subsystem is unique and tailored for the specific medical service provider organization, a lowest tier of the response hierarchy responds to clinical service requests denoted by service identifiers directed toward satisfying general service requests, and each tier in a plurality of subsequent tiers of the organizational processing subsystem is directed to an increasingly specialized group of possible respondents.

45. The system of claim 44, wherein the multi-tiered organizational processing subsystem is configured to process clinical service requests, depending on how various respondents or groups of respondents associated with the multi-tiered organizational processing subsystem are defined, in a hierarchical manner, in a direct manner skipping one or more tiers of the multi-tiered organizational processing subsystem depending on the nature of a clinical service request, in an intra-tier transfer manner between multiple respondents within the same tier level, and/or in a dynamic manner up and/or down the multi-tiered organizational processing subsystem depending on a medical service progression for the clinical service request.

46. The system of claim 44, wherein the multi-tiered organizational processing subsystem is managed by multiple providers with different scopes of practice that are defined by local and/or state regulation.

47. The system of claim 44, wherein the decision support recommendation is transferred directly into an individual's mailbox for processing at a highest tier of the multi-tiered organizational processing subsystem.

48. The system of claim 44, wherein the decision support recommendation is transferred to a regional hub for processing at the lowest tier of the multi-tiered organizational processing subsystem.

49. The system of claim 44, wherein the decision support recommendation is transferred to a processing pool for at least one intermediary tier of the multi-tiered organizational processing subsystem, and the processing pool may include a pharmacy pool, a prescriber pool, a receptionist pool, a medical assistant and/or vocational nurse pool, an administrative pool, a form pool, a local medical service pool, a subspecialty pool, and/or a behavioral health pool.

50. The system of claim 27, wherein the clinical service request is received from at least one of an electronic health records system, a patient portal, a call center, a third-party system, and a professional referral.

51. The system of claim 27, wherein the instructions further cause the device to:

further wherein an operational dashboard is configured to track outputs associated with clinical service requests, and wherein the operational dashboard is configured to update minute by minute, hourly, shift by shift, daily, weekly, and/or monthly to facilitate resource allocation by the medical service provider organization.

* * * * *